(12) United States Patent
Prestrelski

(10) Patent No.: US 9,642,894 B2
(45) Date of Patent: May 9, 2017

(54) COMPOSITIONS FOR RAPIDLY TREATING SEVERE HYPOGLYCEMIA

(71) Applicant: Xeris Pharmaceuticals, Inc., Austin, TX (US)

(72) Inventor: Steven J. Prestrelski, San Diego, CA (US)

(73) Assignee: XERIS PHARMACEUTICALS, INC., Austin, TX (US)

( * ) Notice: Subject to any disclaimer, the term of this patent is extended or adjusted under 35 U.S.C. 154(b) by 0 days.

(21) Appl. No.: 14/676,415

(22) Filed: Apr. 1, 2015

(65) Prior Publication Data

US 2015/0250855 A1  Sep. 10, 2015

Related U.S. Application Data

(63) Continuation of application No. 13/826,662, filed on Mar. 14, 2013, now Pat. No. 9,018,162.

(60) Provisional application No. 61/761,579, filed on Feb. 6, 2013.

(51) Int. Cl.
| | | |
|---|---|---|
| A61K 38/26 | (2006.01) | |
| C07K 14/605 | (2006.01) | |
| A61K 9/00 | (2006.01) | |
| A61K 9/19 | (2006.01) | |

(52) U.S. Cl.
CPC ............ *A61K 38/26* (2013.01); *A61K 9/0019* (2013.01); *A61K 9/19* (2013.01)

(58) Field of Classification Search
CPC ......... A61K 9/19; A61K 9/0019; A61K 38/26
See application file for complete search history.

(56) References Cited

U.S. PATENT DOCUMENTS

| | | | |
|---|---|---|---|
| 3,016,895 A | 1/1962 | Sein | 604/60 |
| 4,608,764 A | 9/1986 | Leuenberger | 34/295 |
| 4,848,094 A | 7/1989 | Davis et al. | 62/64 |
| 4,927,571 A | 5/1990 | Huang et al. | 264/4.3 |
| 5,031,336 A | 7/1991 | Diesner et al. | 34/287 |
| 5,092,843 A | 3/1992 | Monroe et al. | 604/138 |
| 5,208,998 A | 5/1993 | Oyler | 34/288 |
| 5,260,306 A | 11/1993 | Boardman et al. | 514/291 |
| 5,716,640 A | 2/1998 | Kamei et al. | 524/451 |
| 5,932,547 A | 8/1999 | Stevenson et al. | 514/10.3 |
| 5,977,082 A | 11/1999 | Gatti et al. | 514/34 |
| 6,001,336 A | 12/1999 | Gordon | 424/46 |
| 6,051,256 A | 4/2000 | Platz et al. | 424/489 |
| 6,124,261 A | 9/2000 | Stevenson et al. | 514/2.4 |
| 6,199,297 B1 | 3/2001 | Wisniewski | 34/284 |
| 6,253,463 B1 | 7/2001 | Hansen | 34/362 |
| 6,264,990 B1 | 7/2001 | Knepp et al. | 424/499 |
| 6,290,991 B1 | 9/2001 | Roser et al. | 424/502 |
| 6,309,663 B1 | 10/2001 | Patel et al. | 424/450 |
| 6,331,310 B1 | 12/2001 | Roser et al. | 424/423 |
| 6,371,939 B2 | 4/2002 | Bergens et al. | 604/156 |
| 6,495,164 B1 | 12/2002 | Ramstack et al. | 424/489 |
| 6,667,061 B2 | 12/2003 | Ramstack et al. | 424/489 |
| 6,676,958 B2 | 1/2004 | Gerber | 424/434 |
| 6,730,328 B2 | 5/2004 | Maskiewicz et al. | 424/499 |
| 7,005,421 B2 | 2/2006 | Gatti et al. | 514/34 |
| 7,163,704 B2 | 1/2007 | Zhang | 424/725 |
| 7,259,225 B2 | 8/2007 | Song et al. | 528/272 |
| 7,314,636 B2 | 1/2008 | Caseres et al. | 424/426 |
| 7,371,406 B2 | 5/2008 | Ramstack et al. | 424/489 |
| 7,396,841 B2 | 7/2008 | Doen et al. | 514/338 |
| 7,442,832 B2 | 10/2008 | Gentile et al. | 562/460 |
| 7,498,312 B2 | 3/2009 | Cohen et al. | 514/36 |
| 7,582,311 B1 | 9/2009 | Cleland et al. | 424/489 |
| 7,604,822 B2 | 10/2009 | Ionascu | 424/725.1 |
| 7,651,703 B2 | 1/2010 | Cleland et al. | 424/489 |
| 7,915,229 B2 | 3/2011 | Cohen et al. | 514/36 |
| 8,110,209 B2 | 2/2012 | Prestrelski et al. | 424/423 |
| 2002/0179647 A1 | 12/2002 | Hall et al. | 222/175 |
| 2003/0026884 A1 | 2/2003 | Mantius et al. | 426/488 |
| 2003/0119825 A1 | 6/2003 | Folger et al. | 514/226.5 |
| 2003/0170289 A1 | 9/2003 | Chen et al. | 424/426 |
| 2003/0191157 A1 | 10/2003 | Doen et al. | 514/337 |
| 2004/0142043 A1 | 7/2004 | Maeda et al. | 524/499 |

(Continued)

FOREIGN PATENT DOCUMENTS

| | | |
|---|---|---|
| CN | 1507858 | 6/2004 |
| CN | 101842079 | 9/2010 |
| CN | 102164579 | 8/2011 |
| EP | 0 916 347 | 5/1999 |
| EP | 1 502 589 | 2/2005 |
| EP | 2 060 268 | 5/2009 |
| GB | 2 119 248 | 11/1983 |
| WO | WO 91/16882 | 11/1991 |
| WO | WO 94/13344 | 6/1994 |
| WO | WO 95/32730 | 12/1995 |

(Continued)

OTHER PUBLICATIONS

Richards et al, Trehalose: a review of properties, history of use and human tolerance, and results of multiple safety studies, Food and Chemical Toxicology, 2002, 40, pp. 871-898.*

(Continued)

*Primary Examiner* — Julie Ha
*Assistant Examiner* — Li Ni Komatsu
(74) *Attorney, Agent, or Firm* — Norton Rose Fulbright US LLP

(57) ABSTRACT

Disclosed is a composition for parenteral administration comprising a glucagon peptide which has been dried in a non-volatile glycine buffer, and wherein the glucagon peptide has a pH memory that is about equal to the pH of the glucagon peptide in the non-volatile buffer, wherein the pH memory is between 2.5 to 3.5, an aprotic polar solvent, wherein the peptide is solubilized in the aprotic polar solvent, and wherein the aprotic polar solvent is dimethyl sulfoxide (DMSO), trehalose, glycine, and optionally hydrochloric acid, wherein the moisture content of the composition is less than 5 wt. %.

2 Claims, 5 Drawing Sheets

(56) References Cited

U.S. PATENT DOCUMENTS

| | | |
|---|---|---|
| 2004/0176341 A1 | 9/2004 | Chou et al. .................. 514/179 |
| 2005/0019436 A1 | 1/2005 | Burch et al. ................. 424/760 |
| 2005/0069591 A1 | 3/2005 | Bernstein et al. ............ 424/489 |
| 2005/0240166 A1 | 10/2005 | Harper et al. ............. 604/890.1 |
| 2006/0160823 A1 | 7/2006 | Witchey-Lakshmanan et al. ...................... 514/254.07 |
| 2006/0211982 A1 | 9/2006 | Prestrelski et al. ............. 604/60 |
| 2007/0196416 A1 | 8/2007 | Li et al. ........................ 424/422 |
| 2008/0096967 A1 | 4/2008 | Lopez et al. .................. 514/567 |
| 2008/0132493 A1 | 6/2008 | Folger et al. .............. 514/224.2 |
| 2008/0145383 A1 | 6/2008 | Zauner et al. ............. 424/208.1 |
| 2008/0160067 A1 | 7/2008 | Boeckh et al. ............... 424/441 |
| 2008/0200383 A1 | 8/2008 | Jennings et al. ............. 514/11.3 |
| 2008/0220069 A1 | 9/2008 | Allison ......................... 424/489 |
| 2008/0226689 A1 | 9/2008 | Berry et al. .................. 424/423 |
| 2008/0248999 A1 | 10/2008 | Steiner ........................... 514/1.1 |
| 2008/0260840 A1 | 10/2008 | Alessi et al. .................. 424/489 |
| 2008/0305161 A1 | 12/2008 | Shah et al. .................... 424/456 |
| 2009/0143737 A1 | 6/2009 | Kobayashi et al. ..... 604/164.08 |
| 2009/0215883 A1 | 8/2009 | Bouzada et al. .............. 514/449 |
| 2009/0226530 A1 | 9/2009 | Lassner et al. ................ 514/1.1 |
| 2009/0233912 A1 | 9/2009 | Castile et al. ................ 514/220 |
| 2010/0098735 A1 | 4/2010 | Jain et al. ..................... 424/422 |
| 2010/0120660 A1 | 5/2010 | Balschmidt et al. .......... 514/1.1 |
| 2011/0230569 A1 | 9/2011 | Nistor et al. .................. 514/777 |
| 2012/0046225 A1 | 2/2012 | Prestrelski et al. ............ 514/6.8 |
| 2012/0232001 A1 | 9/2012 | Prestrelski et al. ............ 514/5.9 |
| 2013/0123739 A1 | 5/2013 | Yoshikawa ................... 604/408 |
| 2014/0058337 A1 | 2/2014 | Claussen et al. ............. 604/260 |
| 2014/0171362 A1 | 6/2014 | Prestrelski et al. ............ 514/5.9 |
| 2014/0179599 A1 | 6/2014 | Prestrelski et al. ............ 514/6.8 |
| 2014/0179600 A1 | 6/2014 | Prestrelski et al. ............ 514/6.8 |
| 2014/0221288 A1 | 8/2014 | Prestrelski et al. ............ 514/7.2 |
| 2015/0250855 A1 | 9/2015 | Prestrelski et al. ............ 514/6.8 |

FOREIGN PATENT DOCUMENTS

| | | |
|---|---|---|
| WO | WO 96/09814 | 4/1996 |
| WO | WO 98/09613 | 3/1998 |
| WO | WO 98/16250 | 4/1998 |
| WO | WO 98/27963 | 7/1998 |
| WO | WO 00/16829 | 3/2000 |
| WO | WO 01/76682 | 10/2001 |
| WO | WO 01/78687 | 10/2001 |
| WO | WO 02/00137 | 1/2002 |
| WO | WO 02/49660 | 6/2002 |
| WO | WO 03/007782 | 1/2003 |
| WO | WO 03/041684 | 5/2003 |
| WO | WO 03/051398 | 6/2003 |
| WO | WO 2004/037242 | 5/2004 |
| WO | WO 2004/057939 | 7/2004 |
| WO | WO 2004/057959 | 7/2004 |
| WO | WO 2004/091666 | 10/2004 |
| WO | WO 2004/098643 | 11/2004 |
| WO | WO 2005/010079 | 2/2005 |
| WO | WO 2006/031376 | 3/2006 |
| WO | WO 2007/140312 | 12/2007 |
| WO | WO 2008/030469 | 3/2008 |
| WO | WO 2008/041245 | 4/2008 |
| WO | WO 2008/098212 | 8/2008 |
| WO | WO 2008/132224 | 11/2008 |
| WO | WO 2009/045837 | 4/2009 |
| WO | WO 2009/060473 | 5/2009 |
| WO | WO 2009/070298 | 6/2009 |
| WO | WO 2010/018596 | 2/2010 |
| WO | WO 2011/154725 | 12/2011 |
| WO | WO 2012/012460 | 1/2012 |
| WO | WO 2012/122535 | 9/2012 |
| WO | WO 2013/067022 | 5/2013 |

OTHER PUBLICATIONS

Naturally-occurring amino acids, from http://www.benjamin-mills.com/chemistry/amino-acids.htm, pp. 1-5, accessed Jun. 23, 2016.*

Hydrochloric Acid, from http://peoplesrx.com/hydrochloric-acid-the-bodys-primary-digestant/, pp. 1-2, accessed Jun. 23, 2016.*

Administer Intramuscular, Subcutaneous, and Intradermal Injections, from http://www.brooksidepress.org/Products/Administer_IM_SQ_and_ID_Injections/lesson_1 . . . , pp. 1-3, published on 2007.

Amylin Agonists, from http://www.globalrph.com/amylin-agonists.htm, pp. 1-5, accessed Nov. 30, 2014.

Anderson et al., "Revised estimate of the prevalence of multiple sclerosis in the United States", Ann. Neruol, 31(3):333-336, 1992.

Arnon and Aharoni, "Neurogenesis and neuroprotection in the CNS—fundamental elements in the effect of Glatiramer acetate on treatment of autoimmune neurological disorders", Mol. Neurobiol., 36:245-253, 2007.

Autret, E. et al.: "Double-blind, randomized trial of diazepam versus placebo for prevention of recurrence of febrile seizures", The Journal of Pediatrics, vol. 117, No. 3, Sep. 1990, p. 490-494.

Bjartmar and Fox, "Pathological mechanisms and disease progression of multiple sclerosis: therapeutic implications", Drugs of Today, 38:17-29, 2002.

Bornstein et al., "A pilot trial of Cop 1 in exacerbating remitting multiple sclerosis", New Eng. J. Med., 317:408-414, 1987.

Bornstein et al., "A placebo-controlled, double-blind, randomized, two-center, pilot trial of Cop-1 in chronic progressive multiple sclerosis", Neurology, 41:533-539, 1991.

Bromberg, L. et al., "Transport of proteins dissolved in organic solvents across biomimetic membranes", Proceedings of the National Academy of Sciences 92(5):1262-1266, 1995.

Brown: "Clinicians' Guide to Diabetes Gadgets and Gizmos", Clinical Diabetes, 2008, 26, pp. 66-71.

Buffer Reference Center, from http://sigmaaldrich.com/life-science/core-bioreagents/biological-buffers/learningcenter. Accessed Jul. 3, 2013.

Carpenter, et al., "Rational Design of Stable Lyophilized Protein Formulations: Theory and Practice." pp. 1-25. 2002.

Cervera et al, "Mechanism of action of exenatide to reduce postprandial hyperglycemia in type 2 diabetes", Am. J. Physiol. Endocrinol. Metab., 294:E846-E852, 2008.

Chang and Hershenson, "Practical Approaches to Protein Formulation Development", In: Rationale Design of stable protein formulations—theory and practice, pp. 1-25, 2002.

Chang et al., "Development of a Stable Freeze-dried formulation of Recombinant Human Interleukin-1 Receptor Antagonist", Pharmaceutical Research, 13(2):243-249, 1996.

Citric Acid, from http://www.boldsky.com/health/nutrition/2011/natural-citric-acid-sources-030811.html, pp. 1-3, accessed Nov. 26, 2014.

Comi & Filippi, "Treatment with glatiramer acetate delays conversion to clinically definiate multiple sclerosis (CDMS) in patients with clinically isolated syndromes (CIS)", Neurology, 71(2):153, 2008.

Comi et al, "Results from a phase III, one-year, randomized, double-blind, parallel-group, dosecomparison study with glatiramer acetate in relapsing-remitting multiple sclerosis", Mult. Scler., 14(suppl. 1):S299, 2008.

Comi et al., "European/Canadian multicener, double-blind, randomized, placebo-controlled study of the effects of glatiramer acetate on magnetic resonance imaging-measured disease activity and burden in patents with relapsing multiple sclerosis", Ann. Neurol., 49:290-297, 2001.

Compston et al., "The Story of Multiple Sclerosis" In: McAlpine's Multiple Sclerosis. London: Churchill Livingston, pp. 3-42, 2006.

Definition of analog, from http://cancerweb.ncl.ac.uk/cgi-bin/omd?query=analog, pp. 1-5, accessed Jul. 7, 2005.

Definition of mimetic, from http://www.merriam-webster.com/medical/mimetic, p. 1, accessed Jun. 26, 2014.

DeLuca, "Freeze drying of pharmaceuticals", J. Vac. Sci. Technol., 14(1):620, 1977.

Dhib-Jalbut, "Glatirmaer acetate (Copaxone) therapy for multiple sclerosis", Pharmacol Ther., 98:245-255,, 2003.

Dhib-Jalbut, "Mechanisms of action of interferons and glatiramer acetate in multiple sclerosis", Neurology, 25 58(Suppl 4):S3-S9, 2002.

(56) References Cited

OTHER PUBLICATIONS

Diabetes Mellitus—Merck Manual, from http://www.merckmanuals.com/professional/print!endocrine_and_metabolic_disorders/diab . . . , pp. 1-22, accessed Apr. 2, 2013.
DMSO Facts, from http://www.theundergroundcure.com/dmso-facts.html, p. 1, accessed Nov. 26, 2014.
Encyclopedia of Pharmaceutical Technology, vol. 6, Suspensions, pp. 3597-3610, 2007.
Engeloch et al: "Stability of Screening Compounds in Wet DMSO", *Journal of Biomolecular Screening*, 2008, 13, pp. 999-1006.
European Search Report for EP Appl. No. EP 12180169.0 dated Oct. 25, 2012.
Fleming and Carrithers, "Diagnosis and management of multiple sclerosis", Professional communications, Inc., 4 pages, 2002.
Geary and Smith, "Pancreatic Glucagon Fails to Inhibit Sham Feeding in the Rat", Peptides, 1:163-166, 1982.
Glossary of medical education terms, Institute of International Medical Education. http://www.iime.org/glossary.htm. Access in Mar. 2013.
Guideline on clinical investigation of medicinal products for the treatment of multiple sclerosis EMEA, London Sep. 16, 2006.
Human insulin, from http://www.ncbi.nlm.nih/gov/protein/AAA59172.1, p. 1, accessed Nov. 26, 2014.
Hypoglycemia—Merck Manual, from http://web.archive.org/web/20120115004118/http://www.merckmanuals.com/professional/ . . . , pp. 1-2, published on May 2007.
Iasemidis LD, "Epileptic Seizure Prediction and Control." IEEE Transac Biomed Eng. 50:549-558. 2003.
International Search Report and Written Opinion issued in PCT Application PCT/US2013/048293, dated Aug. 8, 2013.
International Search Report and Written Opinion issued in PCT Application PCT/US2011/044576, dated Dec. 14, 2011.
International Search Report and Written Opinion issued in PCT Application PCT/US2012/028621, dated Aug. 22, 2012.
International Search Report and Written Opinion Issued in PCT Application No. PCT/US2014/015123, mailed Apr. 3, 2014.
International Search Report and Written Opinion issued in PCT Application PCT/US2012/062816, dated Jan. 31, 2013.
Johnson et al., "Extended use of glatiramer acetate (Copaxone) is well tolerated and maintains its clinical effect on multiple sclerosis relapse rate and degree of disability", Neurology, 50:701-708, 1998.
Kansara et al., "Subcutaneous delivery", Drug. Deliv. Technol, 9(6):38-42, 2009.
Knudsen, F Ursin; "Recurrence risk after first febrile seizure and effect of short term diazepam prophylaxis", *Archives of Disease in Childhood*, vol. 60, 1985 p. 1045-1049.
Izutsu, Stabilization of Therapeutic Proteins by Chemical and Physical Methods, pp. 287-292, from Therapeutic Proteins Methods and Protocols, Edited by C. Mark Smales and David C. James, published on 2005.

Meyer et al., "Preparation and in vitro characterization of gentamycin-impregnated biodegradable beads suitable for treatment of osteomyelitis", Journal of Pharmaceutical Sciences, 87(9):1149-1154, 1998.
Noseworthy et al, "Multiple sclerosis", New Engl. J. Med., 343:938-952, 2000.
Pellock, John et al.: *Pediatric Epilepsy: Diagnosis and Therapy: Third Edition*—Chapter 19 "Febrile Seizures", 2008, p. 293-301.
Rubiono, Solubilization of Some Poorly Soluble Drug by cosolvents, PhD dissertation, The University of Arizona, 1984.
Ruggiere et al., "Glatiramer acetate in multiple sclerosis: A review", CNS Drug Reviews, 13(2):178-191, 2007.
Shire et al., "Challenges in the development of high protein concentration formulations", J. Pharm. Sci., 93(6):1390-1402, 2004.
Tselis et al., "Glatiramer acetate in the treatment of multiple sclerosis", Neuropsychiatric Dis. Treat. 5Q, 3(2):259-267, 2007.
Wang, "Lyophilization and development of solid protein pharmaceuticals", International Journal of Pharmaceutics, 203:1-60, 2000.
Water, from http://www.biology-online.org/dictionary/Water, pp. 1-3, accessed Apr. 24, 2014.
Weber et al., "Mechanism of action of glatiramer acetate in treatment of multiple sclerosis", Neurotherapeutics, 4(4):647-653, 2007.
Williams and Polli, "The lyophilization of pharmaceuticals: a literature review", Journal of Parenteral Science and Technology, 38(2), 1984.
Wolinsky et al, "Glatiramer acetate in primary progressive multiple sclerosis: Results of a multinationa, multicener, double-blind, placebo-controlled trial", Ann Neurool, 61:14-24, 2007.
Wolinsky, "The use of glatiramer acetate in the treatment of multiple sclerosis", Adv. Neurol., pp. 273-292, 2006.
Zacharis et al., "Volatile buffers can override the 'pH memory' of subtilisin catalysis in organic media", Proc. Natl. Acad. Sci. USA, 96:1201-1205, 1999.
Ziemssen and Schrempf, "Glatiramer acetate: Mechanisms of action in multiple sclerosis", International Rev. of Neurobiol, 79:537-570, 2007.
Vanderweele et al., "Glucagon, Satiety From Feeding and Liver/Pancreatic Interactions," Brain Research Bulletin, 17:539-543 (1986).
International Search Report and Written Opinion issued in PCT/US2015/044060, dated Nov. 2, 2015.
International Search Report and Written Opinion issued in PCT/US2015/014756, dated Sep. 25, 2015.
International Search Report and Written Opinion issued in PCT/US2015/023820, dated Jun. 18, 2015.
Griebel et al.: "SL651498, a GABAA Receptor Agonist with Subtype-Selective Efficacy, as a Potential Treatment for Generalized Anxiety Disorder and Muscle Spasms," CNS Drug Reviews, vol. p, No. 1, pp. 3-20, 2003.

\* cited by examiner

US 9,642,894 B2

COMPOSITIONS FOR RAPIDLY TREATING SEVERE HYPOGLYCEMIA

CROSS-REFERENCE TO RELATED APPLICATIONS

This application is a continuation of U.S. patent application Ser. No. 13/826,662, filed Mar. 14, 2013 (now U.S. Pat. No. 9,018,162), which claims the benefit of U.S. Provisional Application Ser. No. 61/761,579, filed Feb. 6, 2013. The contents of the referenced applications are incorporated into the present application by reference.

BACKGROUND OF THE INVENTION

I. Field of the Invention

The present invention relates generally to pharmaceutical formulations and methods of using the same. More particularly, methods for rapidly treating moderate to severe hypoglycemia in emergency situations or preventing such situations from occurring.

II. Description of the Related Art

Recurrent episodes of severe hypoglycemia not only adversely impacts the quality of life for patients, but also, when severe, can cause seizures, coma, and even death. Severe hypoglycemia is defined as an episode of hypoglycemia that the patient cannot self-treat so that external help is required. Typically, neuroglycopenic symptoms and cognitive impairment begin at a blood glucose level of about 50 mg/dL (2.8 mmol/L), and include cognitive dysfunction that presents as confusion, a slowing of reflexes, the loss of the ability to comprehend and act appropriately, and unpredictable and combative behavior. A blood glucose level below 30 mg/dL may lead to seizures, coma, and death. The seriousness of the situation requires a treatment that responds rapidly, i.e., within 1 to 5 minutes, to prevent the level from falling too far.

Glucagon is a naturally occurring peptide hormone that is 29 amino acids in length and is secreted by the cells of the pancreas. The principal function of glucagon is to maintain glucose production through both glycogenolysis and gluconeogenesis, mostly mediated via the liver. Glucagon is the primary counter-regulatory hormone to insulin and is used as a first-line treatment of hypoglycemia in patients, and particularly those with diabetes. For patients with current or impending hypoglycemia, it is essential to have a treatment that is rapid and easy to administer in an emergency situation or to prevent such an emergency situation from occurring.

Although some progress has been made, there still remains a need for a more user friendly glucagon rescue medication for rapidly treating ongoing or impending hypoglycemia.

SUMMARY OF THE INVENTION

The inventors have discovered a new use for a composition that can be used on a certain subset of patients. Such patients either have severe hypoglycemia or are at risk of imminently developing severe hypoglycemia. In particular, the compositions of the present invention can be used to treat such patients by either maintaining or raising the patient's blood glucose level to a range from 50 mg/dL to 180 mg/dL within a short period of time (e.g., 1 to 5 minutes). As noted above, severe hypoglycemia involves a patient that cannot self-treat so that external help is required (e.g., health care provider such as a doctor or nurse or a mechanical device such as a pump (e.g., bi-hormonal pump)). Such patients typically have blood glucose levels of less than 50 mg/dL and more typically of less than 30 mg/dL. Also, patients that rely on continuous insulin and glucagon administration (e.g., type I or II diabetics) oftentimes monitor and chart their respective blood glucose levels. This monitoring/charting process can be used to identify a downward trend of blood glucose levels as well as the speed or trajectory of this downward trend. In certain situations, the downward trend will lead to hypoglycemia (e.g., blood glucose levels of less than 70, 60, or 50 mg/dL) unless a fast acting composition of glucagon is administered.

In one instance, there is disclosed a method for treating or preventing hypoglycemia in a patient comprising administering an effective amount of a composition comprising (a) a glucagon peptide which has been dried in a non-volatile buffer, and wherein the glucagon peptide has a pH memory that is about equal to the pH of the glucagon peptide in the non-volatile buffer and (b) an aprotic polar solvent, wherein the peptide is solubilized in the aprotic polar solvent, wherein the moisture content of the formulation is less than 5%, and wherein the glucagon peptide maintains the pH memory that is about equal to the pH of the glucagon peptide in the non-volatile buffer when the dried glucagon peptide is reconstituted in the aprotic polar solvent. Prior to administration of the composition, the patient can have severe hypoglycemia (e.g., unable to self-treat or administer such that external help is required (e.g., health care provider such as a doctor or nurse or a mechanical device such as a pump (e.g., bi-hormonal pump)) or be diagnosed as having a blood glucose level of less than 70, 60, 50, 40, 30, 20, 10, 5, or 0 mg/dL or be diagnosed as having a blood glucose level between 0 to 10 mg/dL, 10 to 20 mg/dL, 20 to 30 mg/dL, 30 to 40 mg/dL, 40 to 50 mg/dL, 50 to 60 mg/dL, or 60 to 70 mg/dL, or be diagnosed as having a blood glucose level between 5 to 70 mg/dL, 5 to 60 mg/dL, 5 to 50 mg/dL, 5 to 40 mg/dL, 5 to 30 mg/dL, 5 to 20 mg/dL, or 5 to 10 mg/dL, or be diagnosed as having a blood glucose level of between 10 to 70 mg/dL, 10 to 60 mg/dL, 10 to 50 mg/dL, 10 to 40 mg/dL, or 10 to 30 mg/dL, or be diagnosed as having a blood glucose level of 20 to 70 mg/dL, 20 to 60 mg/dL, 20 to 50 mg/dL, or 20 to 40 mg/dL, or be diagnosed as having a blood glucose level of 30 to 70 mg/dL, 30 to 60 mg/dL, or 30 to 50 mg/dL. Alternatively, and in certain instances, the patient can have a blood glucose level at, around, or greater than 50, 60, 70, 80, 90, 100, 110, 120, 130, 140, 150, 160, 170, 180, 190, or 200 (or any range or integer therein) and also have an indication of impending hypoglycemia or an indication that the blood glucose levels will fall to below 70, 60, or 50 mg/dL within a certain period of time (e.g., within 30, 25, 20, 15, 10, 9, 8, 7, 6, 5, 4, 3, 2, or 1 minute(s). Such an indication can be determined by identifying a downward trend of blood glucose levels (e.g., by a blood glucose monitoring device) as well as the speed or trajectory of this downward trend. In either instance (e.g., the patient is diagnosed with hypoglycemia or is at risk of developing hypoglycemia), administration of the composition to the patient can result in the patient maintaining or increasing the blood glucose level to greater than 50 mg/dL to 180 mg/dL within 1 to 20, 1 to 15, 1 to 10, 1 to 5 or within 1, 2, 3, 4, 5, 6, 7, 8, 9, 10, 11, 12, 13, 14, 15, 16, 17, 18, 19, or 20 minutes after administration of the composition. In a particular aspect, the patient can be diagnosed as having a blood glucose level between 10 mg/dL and less than 40 mg/dL prior to administering the composition. In another instance, the patient's blood glucose level can be determined to be between 50 mg/dL to 70 mg/dL based on the glucose monitoring device and trending downwards in a manner discussed above. In a particular aspect, the patient's blood glucose level can be greater than 50 mg/dL to 180 mg/dL within 1 to 10 minutes or 1 to 5 minutes after administration of the composition. In one aspect, the pH memory of the glucagon peptide can be between 2 to 4, 2.5, to 3.5, or around 3.0. In another aspect, the aprotic polar solvent can be selected from dimethylsulfoxide (DMSO), n-methyl pyrrolidone (NMP), ethyl acetate, and mixtures thereof. DMSO can be used in neat form. The non-volatile buffer can be selected from a glycine buffer, a citrate buffer, a phosphate buffer, and mixtures thereof. In some instances, the non-volatile buffer is a glycine buffer. The amount of the glucagon peptide present in the formulation can be an amount that achieves a desired result. In certain aspects, the amount can range from about 0.5 mg/mL to about 100 mg/mL. The composition can be administered in a variety of ways (e.g., syringe, pen injection device, auto-injector device, pump, etc.) and routes (e.g., parenterally, intravenously, etc.). The patient can be one that has previously been diagnosed as having Type I, Type II, or gestational diabetes). In certain aspects, the composition does not include a protein, peptide, and/or small molecule or other drug substance that is capable of decreasing the blood glucose level in the patient. Examples of peptides that can decrease blood glucose levels include insulin, an insulin mimetic peptide, incretin, or an incretin mimetic peptide. In certain instances, the glucagon is not complexed with a metal ion (e.g., zinc cation). In a particular aspect, the composition can include at least 90% by weight of an aprotic polar solvent and/or 3 to 7% by weight of a carbohydrate. In even further instances, the composition can include between 92 to 96% by weight of an aprotic polar solvent and 4 to 6% by weight of a carbohydrate. In one aspect, the aprotic polar solvent can be DMSO and the carbohydrate can be trehalose.

In some embodiments, the compositions may comprise: (a) a peptide or a salt thereof, wherein the peptide has been dried in a non-volatile buffer, and wherein the dried peptide has a pH memory that is about equal to the pH of the peptide in the non-volatile buffer; and (b) an aprotic polar solvent; wherein the moisture content of the formulation is less than 5%, and wherein the dried peptide maintains the pH memory that is about equal to the pH of the peptide in the non-volatile buffer when the dried peptide is reconstituted in the aprotic polar solvent.

In another aspect, the present invention provides a stable formulation for parenteral injection, the formulation comprising: a peptide or a salt thereof (such as a hydrochloride or acetate salt thereof); and an aprotic polar solvent, wherein the moisture content of the formulation is less than 5%.

In some formulations of the present invention, the peptide is mixed with a non-volatile buffer and a stabilizing excipient, and then dried to a dry peptide powder. Suitable stabilizing excipients include, but are not limited to, sugars, starches, and mixtures thereof. In some embodiments, the sugar is trehalose. In some embodiments, the starch is hydroxyethyl starch (HES). In some embodiments, the stabilizing excipient is present in the formulation in an amount ranging from about 1% (w/v) to about 60% (w/v), from about 1% (w/v) to about 50% (w/v), from about 1% (w/v) to about 40% (w/v), from about 1% (w/v) to about 30% (w/v), from about 1% (w/v) to about 20% (w/v), from about 5% (w/v) to about 60% (w/v), from about 5% (w/v) to about 50% (w/v), from about 5% (w/v) to about 40% (w/v), from about 5% (w/v) to about 30% (w/v), from about 5% (w/v) to about 20% (w/v), from about 10% (w/v) to about 60% (w/v), from about 10% (w/v) to about 50% (w/v), from about 10% (w/v) to about 40% (w/v), from about 10% (w/v) to about 30% (w/v), or from about 10% (w/v) to about 20% (w/v).

Once the peptide or peptides and the non-volatile buffer or the peptide(s), the non-volatile buffer and the stabilizing excipient are dried to a powder, the dried peptide powder is dissolved or reconstituted in an aprotic polar solvent. Examples of aprotic polar solvents include, but are not limited to, the following: dimethylsulfoxide (DMSO), dimethylformamide (DMF), ethyl acetate, n-methyl pyrrolidone (NMP), dimethylacetamide (DMA), propylene carbonate, and mixtures thereof. Dimethylsulfoxide (DMSO), n-methyl pyrrolidone (NMP), ethyl acetate, and mixtures of one or more of DMSO, NMP, and ethyl acetate are particularly preferred aprotic polar solvents. In a preferred embodiment, the aprotic polar solvent is DMSO. In another preferred embodiment, the aprotic polar solvent is a mixture of DMSO and NMP. In yet another preferred embodiment, the aprotic polar solvent is a mixture of DMSO and ethyl acetate.

In some embodiments, the peptide or peptides are reconstituted in a mixture of an aprotic polar solvent (e.g., dimethylsulfoxide (DMSO), dimethylformamide (DMF), ethyl acetate, n-methyl pyrrolidone (NMP), dimethylacetamide (DMA), propylene carbonate, or mixtures thereof) and a co-solvent that depresses the freezing point of the formulation. In some embodiments, the co-solvent depresses the freezing point of the formulation by at least about 5° C., at least about 10° C., at least about 15° C., or at least about 20° C. In some embodiments, the co-solvent depresses the freezing point of the formulation to about 3° C., to about 2° C., to about 1° C., or to about 0° C. or below. In some embodiments, the co-solvent is a polar protic solvent. In preferred embodiments, the co-solvent is selected from ethanol, propylene glycol (PG), glycerol, and mixtures thereof. In some embodiments, the co-solvent is present in the formulation in an amount ranging from about 10% (w/v) to about 50% (w/v), from about 10% (w/v) to about 40% (w/v), from about 10% (w/v) to about 30% (w/v), from about 10% (w/v) to about 25% (w/v), from about 15% (w/v) to about 50% (w/v), from about 15% (w/v) to about 40% (w/v), from about 15% (w/v) to about 30% (w/v), or from about 15% (w/v) to about 25% (w/v).

Importantly, the formulations of the present invention have very little residual moisture and, thus, the peptides in such formulations remain stable over extended periods of time. In preferred embodiments, the moisture content of the formulation of the present invention is less than about 4%, preferably, less than about 3%, preferably, less than about 2%, and even more preferably, less than about 1%, preferably, less than about 0.5%, preferably, less than about 0.25%, preferably, less than about 0.2%, preferably, less than about 0.15%, or preferably, less than about 0.1%. In other preferred embodiments, the moisture content of the formulation of the present invention is from about 0.01% to about 4%, preferably, from about 0.01% to about 3%, preferably, from about 0.01% to about 2%, preferably, from about 0.01% to about 1%, preferably, from about 0.1% to about 4%, preferably, from about 0.1% to about 3%, preferably, from about 0.1% to about 2%, preferably, from about 0.1% to about 1%, preferably, from about 0.25% to about 4%, preferably, from about 0.25% to about 3%, preferably, from about 0.25% to about 2%, preferably, from about 0.25% to about 1%, or preferably, from about 0.5% to about 1%.

When the peptide is mixed with a nonvolatile buffer, the nonvolatile buffer is selected such that the peptide has a pH of maximal stability, maximal solubility, and minimal degradation in the aqueous environment. Once dried, the peptide will have a pH memory of maximal stability, maximal solubility, and minimal degradation and will retain that pH memory when dissolved in or reconstituted in the aprotic polar solvent. As such, in preferred embodiments, the peptide in the formulation will have a pH memory of about 2.0 to about 3.0 to ensure maximal stability, maximal solubility, and minimal degradation. In other embodiments, the peptide in the formulation will have a pH memory of about 3.0 to about 5.0 to ensure maximal stability, maximal solubility, and minimal degradation. In other embodiments, the peptide in the formulation will have a pH memory of about 4.0 to about 5.0 to ensure maximal stability, maximal solubility, and minimal degradation. In yet other embodiments, the peptide will have a pH memory of about 4.0 to about 6.0 to ensure maximal stability, maximal solubility, and minimal degradation. In yet other embodiments, the peptide will have a pH memory of about 6.0 to about 8.0 to ensure maximal stability, maximal solubility, and minimal degradation. It will be readily apparent to one of skill in the art how to determine the optimal pH for obtaining a peptide having maximal stability, maximal solubility, and minimal degradation.

Any suitable dosage of peptide or peptides can be formulated in the stable formulations of the present invention. Generally, the peptide (or, in embodiments comprising two or more peptides, each of the peptides) is present in the formulation in an amount ranging from about 0.5 mg/mL to about 100 mg/mL. In some embodiments, the peptide is present in the formulation in an amount ranging from about 10 mg/mL to about 60 mg/mL. In other embodiments, the peptide is present in the formulation in an amount ranging from about 20 mg/mL to about 50 mg/mL. In still other embodiments, the peptide is present in the formulation in an amount ranging from about 5 mg/mL to about 15 mg/mL. In yet other embodiments, the peptide is present in the formulation in an amount ranging from about 0.5 mg/mL to about 2 mg/mL. In yet other embodiments, the peptide is present in the formulation in an amount ranging from about 1 mg/mL to about 50 mg/mL. Again, it will be readily apparent to those of skill that the peptide dosage can be varied depending on the peptide used and the disease, disorder or condition to be treated.

In some embodiments, the formulations of the present invention further comprise an antioxidant. In other embodiments, the formulations further comprise a chelator. In still other embodiments, the formulations of the present invention further comprise a preservative.

Other objects, features, and advantages of the present invention will be apparent to one of skill in the art from the following detailed description and claims.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION

Figure 1:
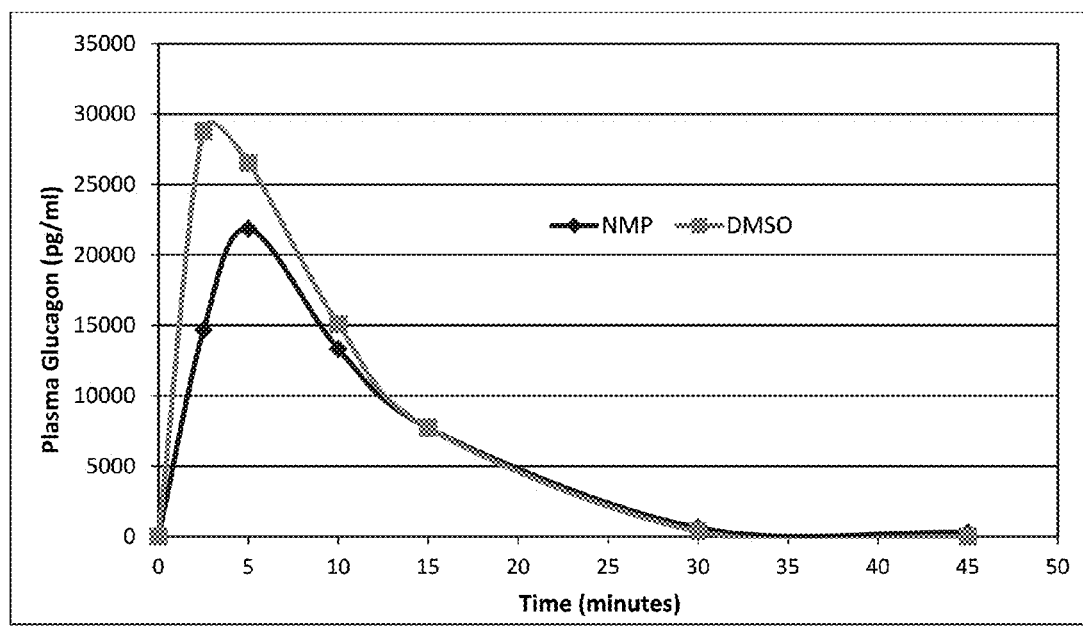
FIG. 1 illustrates plasma glucagon levels after injection of freeze-dried glucagon-glycine-trehalose dissolved in DMSO.

As described above, the inventors discovered a unique property of its formulation that allows for the rapid treatment of hypoglycemia. In particular, it was discovered that severe cases of hypoglycemia can be treated rapidly through administration of the formulations of the present invention to a subject in need of such treatment. Further, the use of glucagon in bi-hormonal insulin-glucagon pumps and closed-loop systems requires that the glucagon component have a rapid onset and depletion to prevent hypoglycemia. These and other non-limiting aspects of the present invention are provided in the following subsections of the present application.

I. Introduction

Peptides can degrade via a number of different mechanisms, including deamidation, oxidation, hydrolysis, disulfide interchange and racemization. Further, water acts as a plasticizer, which facilitates unfolding of protein molecules and irreversible molecular aggregation. Therefore, in order to provide a peptide formulation that is stable over time at ambient or physiological temperatures, a nonaqueous or substantially nonaqueous peptide formulation is generally required.

Reduction of aqueous peptide formulations to dry powdered formulations is one way to increase the stability of pharmaceutical peptide formulations. For example, peptide formulations can be dried using various techniques, including spray-drying, lyophilization or freeze-drying, and desiccation. The dry powder peptide formulations achieved by such techniques exhibit significantly increased stability over time at ambient or even physiological temperatures.

The present invention is based, in part, on the surprising discovery that a stable peptide formulation (e.g., a stable glucagon rescue formulation) can be readily prepared by first freeze-drying one or more peptides (e.g., a glucagon peptide) in a non-volatile buffer to a dry peptide powder. The dried peptide has a defined "pH memory" of the pH of the peptide in the non-volatile buffer from which the peptide was dried. Once dried, the resulting peptide powder, e.g., the freeze-dried glucagon, is dissolved in an aprotic polar solvent, thereby forming a stable formulation, wherein the moisture content of the formulation is less than 5% and, preferably, less than 4%, less than 3%, less than 2%, less than 1%, less than 0.5%, less than 0.25%, less than 0.15%, or less than 0.1%. The dried peptide maintains its defined pH memory when reconstituted in the aprotic polar solvent, i.e., the pH of the peptide when reconstituted in the aprotic polar solvent is about equal to the pH of the peptide in the non-volatile buffer from which it was dried. Advantageously, once prepared, the formulation (e.g., the glucagon formulation) is stable for extended periods of time, is ready for use without the need for reconstitution, and is functional over a range of temperatures.

Importantly, the formulation technology of the present invention is widely applicable for the delivery of numerous other peptides that, like glucagon, have poor or limited stability and solubility in an aqueous environment. In fact, it is now clear that formulation of peptides with an aprotic polar solvent (e.g., DMSO, NMP, ethyl acetate, or a mixture thereof) into high concentration, nonaqueous solutions is an invaluable delivery platform for an important class of therapeutic agents—therapeutic peptides. The stable formulations described herein advantageously promote uniform delivery of the peptide drugs and provide additional shelf stability against aggregation, oxidation, and hydrolysis related degradation pathways.

In certain preferred embodiments, the stable formulations described herein preserve the peptide drugs in a stable form for a prolonged period of time, e.g., for a period of time sufficient to provide a desired shelf life of the formulation without unacceptable levels of degradation of the therapeutic agent prior to use. A desired property of the injectable formulations is that they be nonaqueous and nonreactive with respect to the peptide. In such embodiments, it is possible to store the injectable formulations directly in the injection device itself.

The stable injectable formulations of the present invention contain the necessary delivered dose of therapeutic peptide or peptides (e.g., the dose required for drug therapy) and are preferably low volume. For example, in some embodiments an injectable formulation comprising a therapeutic dose of a peptide (e.g., glucagon) has a volume of at least about 1.0 microliters (the lower limit being a function of the filling equipment), more preferably from about 10 milliliters to about 250 microliters. The delivery of a therapeutic dose of peptide at a low volume is accomplished in certain preferred embodiments by concentrating the dose of the therapeutic peptide or peptides (e.g., glucagon) in a stable form in a suitable aprotic polar solvent for injection in accordance with the invention.

Furthermore, the stable formulations of the present invention are suitable for administration without requiring dilution prior to injection. Many currently available therapeutic peptide and vaccine products are produced in a solid particulate form to promote stability while on the shelf. These formulations are diluted prior to injection in sterile water, phosphate buffer solution, or isotonic saline. In contrast, in certain preferred embodiments of the present invention, the therapeutic peptide is concentrated using the particle preparation processing techniques (e.g., spray drying, lyophilization, etc.) routinely employed by the pharmaceutical industry to prepare formulations for injection. In preferred embodiments, therapeutic dosages of peptide drugs are achieved by dissolving the peptides, which have first been freeze-dried with a non-volatile buffer (and optionally additional components such as a stabilizing excipient) to a dried powder having very little residual moisture content. Once prepared, the dried peptide powder is dissolved in an aprotic polar solvent, such as DMSO, NMP, ethyl acetate, or blends of these solvents. Thus, in accordance with the goals of the present invention, the low volume, stable formulations of the present invention are injected, infused, or otherwise administered into an animal (e.g., human patient), without first diluting the formulation prior to injection as required by most reconstitution products. As such, in preferred embodiments, the low volume formulations of the present invention are administrable without being first being diluted, or reconstituted, or refrigerated.

II. Definitions

For purposes of the present disclosure, the following terms have the following meanings:

The term "therapeutic agent" encompasses peptide compounds together with pharmaceutically acceptable salts thereof. Useful salts are known to those skilled in the art and include salts with inorganic acids, organic acids, inorganic bases, or organic bases. Therapeutic agents useful in the present invention are those peptide compounds that affects a desired, beneficial, and often pharmacological, effect upon administration to a human or an animal, whether alone or in combination with other pharmaceutical excipients or inert ingredients.

The terms "peptide," "polypeptide" and/or "peptide compound" refer polymers of up to about 80 amino acid residues bound together by amide (CONH) linkages. Analogs, derivatives, agonists, antagonists and pharmaceutically acceptable salts of any of the peptide compounds disclosed here are included in these terms. The terms also include peptides and/or peptide compounds that have D-amino acids, modified, derivatized or normaturally occurring amino acids in the D- or L-configuration and/or peptomimetic units as part of their structure.

The term "pharmaceutically acceptable carrier" means a pharmaceutically acceptable solvent, suspending agent or vehicle for delivering a peptide compound of the present invention to a mammal such as an animal or human. In a presently preferred embodiment, the pharmaceutically acceptable carrier is an aprotic polar solvent.

The term "aprotic polar solvent" means a polar solvent that does not contain acidic hydrogen and does not act as a hydrogen bond donor. Examples of aprotic polar solvents include, but are not limited to, dimethylsulfoxide (DMSO), dimethylformamide (DMF), ethyl acetate, n-methyl pyrrolidone (NMP), dimethylacetamide (DMA), and propylene carbonate. The term aprotic polar solvent also encompasses mixtures of two or more aprotic polar solvents, e.g., a mixture of two or more of dimethylsulfoxide (DMSO), dimethylformamide (DMF), ethyl acetate, n-methyl pyrrolidone (NMP), dimethylacetamide (DMA), and propylene carbonate.

The term "pharmaceutically acceptable" ingredient, excipient or component is one that is suitable for use with humans and/or animals without undue adverse side effects (such as toxicity, irritation and allergic response) commensurate with a reasonable benefit/risk ratio.

The term "chemical stability" means that with respect to the therapeutic agent, an acceptable percentage of degradation products produced by chemical pathways such as oxidation or hydrolysis is formed. In particular, a formulation is considered chemically stable if no more than about 20% breakdown products are formed after one year of storage at the intended storage temperature of the product (e.g., room temperature); or storage of the product at 30° C./60% relative humidity for one year; or storage of the product at 40° C./75% relative humidity for one month, and preferably three months. In some embodiments, a chemically stable formulation has less than 20%, less than 15%, less than 10%, less than 5%, less than 4%, less than 3%, less than 2%, or less than 1% breakdown products formed after an extended period of storage at the intended storage temperature of the product.

The term "physical stability" means that with respect to the therapeutic agent, an acceptable percentage of aggregates (e.g., dimers, trimers and larger forms) is formed. In particular, a formulation is considered physically stable if no more that about 15% aggregates are formed after one year of storage at the intended storage temperature of the product (e.g., room temperature); or storage of the product at 30° C./60% relative humidity for one year; or storage of the product at 40° C./75% relative humidity for one month, and preferably three months. In some embodiments, a physically stable formulation has less than less than 15%, less than 10%, less than 5%, less than 4%, less than 3%, less than 2%, or less than 1% aggregates formed after an extended period of storage at the intended storage temperature of the product.

The term "stable formulation" means that at least about 65% chemically and physically stable therapeutic agent remains after two months of storage at room temperature. Particularly preferred formulations are those in which at least about 80%, 85%, 90%, 91%, 92%, 93%, 94%, 95%, 96%, 97%, 98%, or 99% chemically and physically stable therapeutic agent remains under these storage conditions. Especially preferred stable formulations are those which do not exhibit degradation after sterilizing irradiation (e.g., gamma, beta or electron beam).

The phrase "consisting essentially of" is used herein to exclude any elements that would substantially alter the essential properties of the stable formulations to which the phrase refers.

The term "bioavailability" is defined for purposes of the present invention as the extent to which the therapeutic agent, such as a peptide compound, is absorbed from the formulation.

The term "systemic" means, with respect to delivery or administration of a therapeutic agent, such as a peptide compound, to a subject, that therapeutic agent is detectable at a biologically significant level in the blood plasma of the subject.

The term "controlled release" is defined for purposes of the present invention as the release of the therapeutic agent at such a rate that blood (e.g., plasma) concentrations are maintained within the therapeutic range, but below toxic concentrations over a period of time of about one hour or longer, preferably 12 hours or longer.

The term "parenteral injection" refers to the administration of therapeutic agents, such as peptide compounds, via injection under or through one or more layers of skin or mucus membranes of an animal, such as a human. Standard parenteral injections are given into the intradermal, subcutaneous, or intramuscular region of an animal, e.g., a human patient. In some embodiments, a deep location is targeted for injection of a therapeutic agent as described herein.

The terms "treat" or "treatment" refer to delaying the onset of, retarding or reversing the progress of, or alleviating or preventing either the disease or condition to which the term applies, or one or more symptoms of such disease or condition.

The terms "patient," "subject," or "individual" interchangeably refer to a mammal, for example, a human or a non-human mammal, e.g., a primate, dog, cat, bovine, ovine, porcine, equine, mouse, rat, hamster, rabbit, or guinea pig.

III. Stable Peptide Formulations

In one aspect, the present invention provides a stable formulation for parenteral injection. Advantageously, once prepared, the formulation is stable for extended periods of time, is ready for use without the need for reconstitution, and is functional over a range of temperatures. Furthermore, the stable formulation of the present invention is useful for the parenteral injection of any peptide that has limited or poor stability or solubility in an aqueous environment. In some embodiments, the formulations of the present invention increase the physical stability of the peptide or peptides of the formulation, for example, by preventing or decreasing the formation of aggregates of the peptide or peptides.

In some embodiments, the formulation comprises: (a) a peptide or a salt thereof, wherein the peptide has been dried in a non-volatile buffer, and wherein the dried peptide has a pH memory that is about equal to the pH of the peptide in the non-volatile buffer; and (b) an aprotic polar solvent; wherein the moisture content of the formulation is less than 5%, and wherein the dried peptide maintains the pH memory that is about equal to the pH of the peptide in the non-volatile buffer when the dried peptide is reconstituted in the aprotic polar solvent.

In some embodiments, the formulation comprises: (a) a first peptide or a salt thereof, wherein the first peptide has been dried in a first non-volatile buffer, and wherein the first dried peptide has a first pH memory that is about equal to the pH of the first peptide in the first non-volatile buffer; (b) a second peptide or a salt thereof, wherein the second peptide has been dried in a second non-volatile buffer, and wherein the second dried peptide has a second pH memory that is about equal to the pH of the second peptide in the second non-volatile buffer; and (c) an aprotic polar solvent; wherein the moisture content of the formulation is less than 5%, wherein the first dried peptide maintains the first pH memory that is about equal to the pH of the first peptide in the first non-volatile buffer when the first dried peptide is reconstituted in the aprotic polar solvent, and wherein the second dried peptide maintains the second pH memory that is about equal to the pH of the second peptide in the second non-volatile buffer when the second dried peptide is reconstituted in the aprotic polar solvent.

In some embodiments, the formulation consists essentially of: (a) a peptide or a salt thereof, wherein the peptide has been dried in a non-volatile buffer, and wherein the dried peptide has a pH memory that is about equal to the pH of the peptide in the non-volatile buffer; and (b) an aprotic polar solvent; wherein the moisture content of the formulation is less than 5%, and wherein the dried peptide maintains the pH memory that is about equal to the pH of the peptide in the non-volatile buffer when the dried peptide is reconstituted in the aprotic polar solvent.

A. Peptides

The stable formulations of the present invention comprise one, two, three, four, or more peptides or salts, analogs, and/or mixtures thereof. Peptides (as well as salts thereof) suitable for use in the formulations of the present invention include, but are not limited to, glucagon, pramlintide, insulin, leuprolide, an luteinizing-hormone-releasing hormone (LHRH) agonist, parathyroid hormone (PTH), amylin, botulinum toxin, hematide, an amyloid peptide, cholecystikinin, gastric inhibitory peptide, an insulin-like growth factor, growth hormone releasing factor, anti-microbial factor, glatiramer, glucagon-like peptide-1 (GLP-1), a GLP-1 agonist, exenatide, analogs thereof, and mixtures thereof. In some embodiments, the peptide is a hydrochloride salt or an acetate salt.

In a preferred embodiment, the peptide is glucagon or a glucagon analog or peptidomimetic, or a salt thereof (e.g., glucagon acetate). In another embodiment, the peptide is parathyroid hormone. In yet another embodiment, the peptide is leuprolide. In still another embodiment, the peptide is glatiramer. In other embodiments, the peptide is amylin or an amylinomimetic (e.g., pramlintide). In still other embodiments, the peptide is insulin or an insulin analog (e.g., Lispro). In some embodiments, the insulin or insulin analog preparation is a low-zinc or zinc-free preparation.

In some embodiments, the formulation comprises two peptides, wherein the first peptide is amylin or an amylinomimetic and the second peptide is insulin or an insulin analog. In some embodiments, the first peptide is pramlintide and the second peptide is insulin. In some embodiments, the first peptide is pramlintide and the second peptide is a low-zinc insulin preparation or a zinc-free insulin preparation.

In some embodiments, the formulation comprises two peptides, wherein the first peptide is glucagon and the second peptide is a glucagon-like peptide-1 (GLP-1) or a GLP-1 analog or agonist (e.g., exenatide). In some embodiments, the first peptide is glucagon and the second peptide is GLP-1. In some embodiments, the first peptide is glucagon and the second peptide is exenatide.

Any suitable dosage of peptide or peptides can be administered using the formulations of the present invention. The dosage administered will, of course, vary depending upon known factors, such as the pharmacodynamic characteristics of the particular peptide, salt, or combination thereof; the age, health, or weight of the subject; the nature and extent of symptoms; the metabolic characteristics of the therapeutic agent and patient, the kind of concurrent treatment; the frequency of treatment; or the effect desired. Generally, the peptide (or, wherein the stable formulation comprises two or more peptides, each of the peptides) is present in the formulation in an amount ranging from about 0.5 mg/mL to about 100 mg/mL (e.g., about 0.5, 1, 2, 3, 4, 5, 6, 7, 8, 9, 10, 15, 20, 25, 30, 35, 40, 45, 50, 55, 60, 65, 70, 75, 80, 85, 90, 95, or 100 mg/mL).

In some embodiments, the peptide is present in the formulation in an amount ranging from about 0.5 mg/mL to about 60 mg/mL. In some embodiments, the peptide is present in the formulation in an amount ranging from about 10 mg/mL to about 50 mg/mL. In other embodiments, the peptide is present in the formulation in an amount ranging from about 20 mg/mL to about 50 mg/mL. In still other embodiments, the peptide is present in said formulation in an amount ranging from about 5 mg/mL to about 15 mg/mL. In yet other embodiments, the peptide is present in the formulation in an amount ranging from about 0.5 mg/mL to about 2 mg/mL. Again, it will be readily apparent to those of skill that the peptide dosage can be varied depending on the peptide used and the disease, disorder or condition to be treated.

In preferred embodiments, the peptide is mixed with a non-volatile buffer, and optionally a stabilizing excipient, and then dried to a dry peptide powder. In embodiments where the stable formulation comprises two or more peptides, each of the peptides is separately mixed with a non-volatile buffer, and optionally a stabilizing excipient, and then dried to a dry peptide powder. Peptides are susceptible to hydrolysis at bonds with asparagine residues and oxidation of methionine, so the use of non-volatile buffers in the formulations of the present invention beneficially affects chemical stability. As described in further detail below, while pH is not relevant in an aprotic polar solvent, the charge profile of a peptide in an aprotic polar solvent will affect its stability. The charge profile of a peptide in an aprotic polar solvent will be a function of the pH of the aqueous solution from which it was previously dried, i.e., there is a "pH memory" after dissolution or reconstitution in an aprotic polar solvent. To achieve the desired charge profile for a peptide dissolved in an aprotic polar solvent, the peptide is dried from a buffered aqueous solution at the pH that yields the optimal stability, optimal solubility, and minimal degradation in the aprotic polar solvent.

As such, non-volatile buffers that are useful in the formulations described herein are those that are helpful in establishing a pH of maximum stability, maximum solubility, and minimal degradation as well as those that are helpful in removing residual moisture or water content from the dried peptide powder. Non-volatile buffers include those buffers that will not evaporate away in a manner similar to water upon drying/lyophilization. Suitable non-volatile buffers include, for example, glycine buffers, citrate buffers, phosphate buffers, and mixtures thereof. In some embodiments, the non-volatile buffer is a glycine buffer or a citrate buffer. In some embodiments, the non-volatile buffer is a glycine buffer. In some embodiments, the non-volatile buffer is a mixture of glycine buffer and citrate buffer. In some embodiments, the non-volatile buffer is a mixture of citrate buffer and phosphate buffer.

B. Stabilizing Excipients

In certain preferred embodiments, the formulations described herein may be further stabilized to ensure the stability of the peptide incorporated therein. In some embodiments, the stability of the injectable formulation is enhanced by the inclusion of one or more stabilizing agents or stabilizing excipients into the formulation prior to the drying of the peptide or peptides. In other embodiments, the stability of the injectable formulation is enhanced by reconstituting the dried peptide or peptides with a stabilizing agent or stabilizing excipient in the aprotic polar solvent.

In some embodiments, the stabilizing excipient is a cryoprotectant. As shown below in the Examples section, the addition of a cryoprotectant, such as trehalose, protects the peptide formulations of the present invention against instability associated with freeze-thaw cycles. Furthermore, it has been shown herein that the addition of the cryoprotectant trehalose also promotes enhanced thawing of a frozen peptide formulation. This property of enhanced thawing is surprisingly advantageous, particularly in emergency medical situations, such as a severe hypoglycemia episode, wherein a peptide formulation of the present invention is frozen and needs to be administered quickly. Thus, in another aspect of the present invention, the stable formulation has an improved freeze-thaw stability, an enhanced thawing rate, and/or an enhanced thawing profile.

In some embodiments, the stabilizing excipient is selected from sugars, starches, sugar alcohols, and mixtures thereof. Examples of suitable sugars for stabilizing excipients include, but are not limited to, trehalose, glucose, sucrose, etc. Examples of suitable starches for stabilizing excipients include, but are not limited to, hydroxyethyl starch (HES). Examples of suitable sugar alcohols for stabilizing excipients include, but are not limited to, mannitol and sorbitol. In some embodiments, the at least one stabilizing excipient (e.g., a sugar, a starch, a sugar alcohol, or a mixture thereof) is capable of enhancing the stability of the peptide during a freeze-thawing process, enhancing the thawing rate of the formulation, or enhancing the thawing profile of the formulation.

In some embodiments, the stabilizing excipient is present in the formulation in an amount ranging from about 1% (w/v) to about 60% (w/v), from about 1% (w/v) to about 50% (w/v), from about 1% (w/v) to about 40% (w/v), from about 1% (w/v) to about 30% (w/v), from about 1% (w/v) to about 20% (w/v), from about 5% (w/v) to about 60% (w/v), from about 5% (w/v) to about 50% (w/v), from about 5% (w/v) to about 40% (w/v), from about 5% (w/v) to about 30% (w/v), from about 5% (w/v) to about 20% (w/v), from about 10% (w/v) to about 60% (w/v), from about 10% (w/v) to about 50% (w/v), from about 10% (w/v) to about 40% (w/v), from about 10% (w/v) to about 30% (w/v), or from about 10% (w/v) to about 20% (w/v). In some embodiments, the stabilizing excipient is present in the formulation in an amount that is about 1%, about 5%, about 10%, about 15%, about 20%, about 25%, about 30%, about 35%, about 40%, about 45%, about 50%, about 55%, or about 60% (w/v).

In formulations comprising two or more peptides, in some embodiments each of the peptides are dried in a mixture comprising a non-volatile buffer and a stabilizing excipient. The mixtures of the non-volatile buffer and the stabilizing excipient may be the same for each peptide, or the non-volatile buffer, the stabilizing excipient, or both the non-volatile buffer and stabilizing excipient that is used for drying each peptide may be different. In other embodiments, some but not all of the peptides may be dried in a mixture comprising a non-volatile buffer and a stabilizing excipient, while other peptides may be dried in a non-volatile buffer in the absence of a stabilizing excipient.

In some embodiments, the formulation further comprises additional stabilizing agents including, for example, antioxidants, chelators and preservatives. Examples of suitable antioxidants include, but are not limited to, ascorbic acid, cysteine, methionine, monothioglycerol, sodium thiosulphate, sulfites, BHT, BHA, ascorbyl palmitate, propyl gallate, N-acetyl-L-cysteine (NAC), and Vitamin E. Examples of suitable chelators include, but are not limited to, EDTA, tartaric acid and salts thereof, glycerin, and citric acid and salts thereof. Examples of suitable preservatives include, but are not limited to, benzyl alcohols, methyl parabens, propyl parabens, and mixtures thereof.

In some embodiments, the formulation further comprises a stabilizing polyol. Such formulations and materials are described, for example, in U.S. Pat. Nos. 6,290,991 and 6,331,310, the contents of each of which are incorporated by reference herein.

C. Reconstitution of Dried Peptides

In the stable formulations of the present invention, once the peptide and non-volatile buffer (and optionally the stabilizing excipient) are dried to a powder, or where the formulation comprises two or more peptides, once each of the peptide and non-volatile buffer (each optionally also comprising a stabilizing excipient) is dried to a powder, the dried peptide powder is, or the dried peptide powders are, dissolved or reconstituted in an aprotic polar solvent. In some embodiments, the aprotic polar solvent is selected from dimethylsulfoxide (DMSO), dimethylformamide (DMF), ethyl acetate, n-methyl pyrrolidone (NMP), dimethylacetamide (DMA), propylene carbonate, and mixtures thereof. In some embodiments, the aprotic polar solvent is a mixture of two or more of dimethylsulfoxide (DMSO), dimethylformamide (DMF), ethyl acetate, n-methyl pyrrolidone (NMP), dimethylacetamide (DMA), and propylene carbonate. Dimethylsulfoxide (DMSO), ethyl acetate, and n-methyl pyrrolidone (NMP) are particularly preferred aprotic polar solvents, each of which is a biocompatible solvent. In some embodiments, the aprotic polar solvent is dimethylsulfoxide (DMSO). In other embodiments, the aprotic polar solvent is n-methyl pyrrolidone (NMP). In other embodiments, the aprotic polar solvent is a mixture of dimethylsulfoxide (DMSO) and n-methyl pyrrolidone (NMP). In still other embodiments, the aprotic polar solvent is a mixture of dimethylsulfoxide (DMSO) and ethyl acetate. In some embodiments, the dried peptide powder is reconstituted in an aprotic polar solvent that is "neat," i.e., that does not contain a co-solvent. In some embodiments, the dried peptide powder is reconstituted in a solution that comprises an aprotic polar solvent and that does not contain water as a co-solvent.

In some embodiments, the formulations of the present invention further comprise at least one co-solvent that depresses the freezing point of the formulation. The co-solvent is a polar protic solvent. In some embodiment, the co-solvent is selected from ethanol, propylene glycol (PG), glycerol, and mixtures thereof. In some embodiments, the co-solvent is ethanol or propylene glycol (PG). The co-solvent may be present in the formulation in an amount ranging from about 10% (w/v) to about 50% (w/v), e.g., about 10%, about 15%, about 20%, about 25%, about 30%, about 35%, about 40%, about 45%, or about 50% (w/v). In some embodiments, the co-solvent is present in the formulation in an amount ranging from about 10% (w/v) to about 50% (w/v), from about 10% (w/v) to about 40% (w/v), from about 10% (w/v) to about 30% (w/v), from about 10% (w/v) to about 25% (w/v), from about 15% (w/v) to about 50% (w/v), from about 15% (w/v) to about 40% (w/v), from about 15% (w/v) to about 30% (w/v), or from about 15% (w/v) to about 25% (w/v). In some embodiments, the at least one co-solvent depresses the freezing point of the formulation by at least 5° C., at least 10° C., at least 15° C., at least 20° C. or more as compared to an otherwise identical formulation that does not comprise the co-solvent. In some embodiments, the at least one co-solvent depresses the freezing point of the formulation to about 3° C., to about 2° C., to about 1° C., or to about 0° C. or below.

D. Moisture Content

The formulations of the present invention have very little residual moisture and, thus, the peptides in such formulations remain stable over extended periods of time. In some embodiments, the stable formulations of the present invention have a moisture content that is less than 5%. In some embodiments, the moisture content is less than 4%, less than 3%, less than 2%, less than 1%, less than 0.5%, less than 0.4%, less than 0.3%, less than 0.25%, less than 0.2%, less than 0.15%, less than 0.1%, less than 0.075%, less than 0.05%, less than 0.025%, or less than 0.01%. In some preferred embodiments, the moisture content of the formulations of the present invention is from about 0.01% to about 5%, from about 0.01% to about 4%, from about 0.01% to about 3%, from about 0.01% to about 2%, from about 0.01% to about 1.5%, or from about 0.01% to about 1%. In other preferred embodiments, the moisture content of the formulations of the present invention is from about 0.1% to about 5%, from about 0.1% to about 4%, from about 0.1% to about 3%, from about 0.1% to about 2%, from about 0.1% to about 1.5%, or from about 0.1% to about 1%. In other preferred embodiments, the moisture content of the formulations of the present invention is from about 0.25% to about 5%, from about 0.25% to about 4%, from about 0.25% to about 3%, from about 0.25% to about 2%, or from about 0.25% to about 1.5%. In still other preferred embodiments, the moisture content of the formulations is from about 0.5% to about 1%.

E. pH Memory

The "pH memory" of a peptide is the resulting charge profile (protonation state) after drying the peptide from a buffered aqueous solution (e.g., from a non-volatile buffer). The protonation state, and thus the solubility and stability of peptides, in very low or zero moisture non-aqueous solvents are affected by the aqueous pH of the peptide solution before drying and the drying conditions employed. When the peptide is dried in a buffer species in which both the acidic and basic components are non-volatile, the pH memory of the dried peptide will be about equal to the pH of the peptide in the non-volatile buffer. See, e.g., Enzymatic Reactions in Organic Media, Koskinen, A. M. P., and Klibanov, A. M., eds., Springer (1996). Furthermore, the pH of the buffered aqueous solution (e.g., non-volatile buffer) in which the peptide is dried can be optimized to yield a pH memory for the peptide that results in optimal peptide stability, maximum solubility, and minimal degradation when the dried peptide is subsequently reconstituted in an aprotic polar solvent. Because aprotic polar solvents do not have exchangeable protons, when the dried peptide is reconstituted into an aprotic polar solvent, the reconstituted formulation will maintain the solubility and stability characteristics of the optimal pH memory.

For stable formulations comprising two, three, four, or more peptides, each peptide is dried so that it has its own pH memory that is optimized for maximum solubility, maximum stability, and minimal degradation. In embodiments where there are two or more peptides in the formulation, the pH memory range of the first peptide may partially overlap with the pH memory range of the second peptide (e.g., the pH memory of the first peptide may be from about 4.0 to about 6.0, and the pH memory of the second peptide may be from about 6.0 to about 8.0), or the pH memory range of the first peptide may not overlap with the pH memory range of the second peptide (e.g., the pH memory of the first peptide may be from about 4.0 to about 5.0, and the pH memory of the second peptide may be from about 6.0 to about 8.0).

The pH memory of a peptide can be measured in several ways. In one method, the pH memory of a peptide is measured by reconstituting the dried peptide into un-buffered water and measuring the pH of the reconstituted peptide with a pH indicator such as pH paper or a calibrated pH electrode. Alternatively, the pH memory of a peptide can be determined for a peptide that has been reconstituted in the aprotic polar solvent (e.g., DMSO) by adding at least 20% water to the aprotic polar solvent (e.g., DMSO) and measuring the pH with a pH indicator. See, e.g., Baughman and Kreevoy, "Determination of Acidity in 80% Dimethyl Sulfoxide-20% Water," Journal of Physical Chemistry, 78(4): 421-23 (1974). Measurement of pH in an aprotic polar solvent-water solution may require a small correction (i.e., no more than 0.2 pH unit as per Baughman and Kreevoy, supra).

In some embodiments, a dried peptide has a pH memory that is about equal to the pH of the peptide in the non-volatile buffer from which it was dried when the pH memory of the peptide when it is reconstituted in an aprotic polar solvent is within one pH unit of the pH of the peptide in the non-volatile buffer from which it is dried (thus, for example, for a peptide having a pH of 3.0 in the non-volatile buffer from which the peptide is dried, a pH memory for the peptide of from 2.0 to 4.0, when reconstituted in the aprotic polar solvent, would be within one pH unit, and thus the pH memory of the dried peptide would be about equal to the pH of the peptide in the non-volatile buffer). In some embodiments, a dried peptide has a pH memory that is about equal to the pH of the peptide in the non-volatile buffer from which it was dried when the pH memory of the peptide when it is reconstituted in an aprotic polar solvent is within half of a pH unit of the pH of the peptide in the non-volatile buffer from which it is dried (thus, for example, for a peptide having a pH of 3.0 in the non-volatile buffer from which the peptide is dried, a pH memory for the peptide of from 2.5 to 3.5, when reconstituted in the aprotic polar solvent, would be within half of a pH unit, and thus the pH memory of the dried peptide would be about equal to the pH of the peptide in the non-volatile buffer).

In some embodiments, the peptide of the stable formulation has a pH memory of about 1.5 to about 2.5. In some embodiments, the peptide of the stable formulation has a pH memory of about 2.0 to about 3.0. In some embodiments, the peptide of the stable formulation has a pH memory of about 2.0 to about 4.0. In some embodiments, the peptide of the stable formulation has a pH memory of about 2.5 to about 4.0. In some embodiments, the peptide of the stable formulation has a pH memory of about 2.5 to about 3.5. In some embodiments, the peptide of the stable formulation has a pH memory of about 3.0 to about 5.0. In some embodiments, the peptide of the stable formulation has a pH memory of about 3.0 to about 4.5. In some embodiments, the peptide of the stable formulation has a pH memory of about 4.0 to about 5.0. In some embodiments, the peptide of the stable formulation has a pH memory of about 4.0 to about 6.0. In some embodiments, the peptide of the stable formulation has a pH memory of about 6.0 to about 8.0. In some embodiments, the peptide of the stable formulation has a pH memory of about 6.5 to about 8.0. In some embodiments, the peptide of the stable formulation has a pH memory of about 6.5 to about 7.5. In some embodiments, the peptide of the stable formulation has a pH memory of about 6.5 to about 9.0. In some embodiments, the peptide of the stable formulation has a pH memory of about 7.0 to about 9.0. In some embodiments, the peptide of the stable formulation has a pH memory of about 7.5 to about 9.0. In some embodiments, the peptide of the stable formulation has a pH memory of about 8.0 to about 10.0. In some embodiments, the peptide of the stable formulation has a pH memory of about 8.5 to about 10.0. In some embodiments, the pH memory of a peptide may be about 1.5, about 2.0, about 2.5, about 3.0, about 3.5, about 4.0, about 4.5, about 5.0, about 5.5, about 6.0, about 6.5, about 7.0, about 7.5, about 8.0, about 8.5, about 9.0, about 9.5, or about 10.0.

F. Exemplary Formulations

In some particular embodiments, the present invention provides a stable glucagon formulation, the glucagon formulation comprising: a glucagon peptide or salt thereof (e.g., glucagon acetate), wherein the glucagon has been dried in a non-volatile buffer selected from a glycine buffer, a citrate buffer, a phosphate buffer, and mixtures thereof, and wherein the dried glucagon has a pH memory that is from about 2.0 to about 3.0; and an aprotic polar solvent selected from the group consisting of dimethylsulfoxide (DMSO), ethyl acetate, n-methyl pyrrolidone (NMP), and mixtures thereof; wherein the moisture content of the formulation is less than 5%, and wherein the dried glucagon maintains the pH memory of about 2.0 to about 3.0 when the dried glucagon is reconstituted in the aprotic polar solvent. In some embodiments, the glucagon is present in the formulation in an amount ranging from about 0.5 mg/mL to about 100 mg/mL, or from about 1 mg/mL to about 50 mg/mL. In some embodiments, the moisture content of the formulation is less than about 2%, less than about 1%, less than about 0.5%, or less than about 0.01%. In some embodiments, the moisture content of the formulation is from about 0.01% to about 3%. In some embodiments, the formulation further comprises a stabilizing excipient selected from sugars (e.g., trehalose), starches (e.g., hydroxyethyl starch (HES)), and mixtures thereof. The stabilizing excipient may be present in the formulation in an amount ranging from about 1% (w/v) to about 60% (w/v). In some embodiments, the formulation further comprises a co-solvent that depresses the freezing point of the formulation, wherein the co-solvent is selected from ethanol, propylene glycol, glycerol, and mixtures thereof. The co-solvent may be present in the formulation in an amount ranging from about 10% (w/v) to about 50% (w/v).

In other particular embodiments, the present invention provides a stable glucagon formulation, the glucagon formulation comprising: a glucagon peptide or salt thereof (or glucagon analog or peptidomimetic); and an aprotic polar solvent selected from the group consisting of dimethylsulfoxide (DMSO), n-methyl pyrrolidone (NMP) and mixtures thereof; wherein the moisture content of the formulation is less than 3%. In preferred embodiments, the moisture content of the formulation is less than 2%, less than 1%, less than 0.5% and less than 0.25%. In other preferred embodiments, the moisture content is from 0.25% to about 3%, preferably from about 0.25% to about 2%, more preferably from about 0.25% to about 1.5%, more preferably from about 0.25% to about 1%, more preferably from about 0.5% to about 1%.

In other particular embodiments, the stable glucagon formulation further comprises a non-volatile buffer and a stabilizing excipient that is a sugar, a starch, or a sugar alcohol. For instance, in some embodiments, the glucagon formulation further comprises a glycine buffer and mannitol, or a citrate buffer and mannitol, or a phosphate buffer and mannitol. In some embodiments, the glucagon formulation further comprises a glycine buffer and trehalose, or a citrate buffer and trehalose, or a phosphate buffer and trehalose. In these embodiments, the aprotic polar solvent can be DMSO, NMP, ethyl acetate, or a mixture thereof. For instance, in one preferred embodiment, the aprotic polar solvent is DMSO, and the non-volatile buffer is a glycine buffer. In another preferred embodiment, the aprotic polar solvent is DMSO, the non-volatile buffer is a citrate buffer and the stabilizing excipient is mannitol. In another preferred embodiments, the aprotic polar solvent is DMSO, the non-volatile buffer is a glycine buffer, and the stabilizing excipient is trehalose. In still another preferred embodiment, the aprotic polar solvent is DMSO, and the non-volatile buffer is a citrate buffer. In still another preferred embodiment, the aprotic polar solvent is NMP, and the non-volatile buffer is a glycine buffer.

In other particular embodiments, the present invention provides a stable formulation comprising: glucagon or a salt thereof (e.g., glucagon acetate), wherein the glucagon has been dried in a non-volatile buffer, and wherein the dried glucagon has a pH memory that is about equal to the pH of the glucagon in the non-volatile buffer selected from a glycine buffer, a citrate buffer, a phosphate buffer, and mixtures thereof, wherein the pH memory of the dried glucagon is from about 2.0 to about 3.0; and an aprotic polar solvent selected from dimethylsulfoxide (DMSO), n-methyl pyrrolidone (NMP), ethyl acetate, and mixtures thereof; wherein the moisture content of the formulation is less than 1%, and wherein the dried glucagon maintains the pH memory that is about equal to the pH of the glucagon in the non-volatile buffer when the dried glucagon is reconstituted in the aprotic polar solvent. In some embodiments, the glucagon formulation further comprises a co-solvent that depresses the freezing point of the formulation, wherein the co-solvent is selected from ethanol, propylene glycol, glycerol, and mixtures thereof. In some embodiments, the glucagon formulation further comprises a stabilizing excipient selected from sugars, starches, and mixtures thereof. In some embodiments, the glucagon is present in the formulation in an amount ranging from about 1 mg/mL to about 50 mg/mL.

In other particular embodiments, the present invention provides a stable glucagon formulation, the glucagon formulation consisting essentially of: a glucagon peptide or salt thereof (e.g., glucagon acetate), wherein the glucagon has been dried in a non-volatile buffer selected from a glycine buffer, a citrate buffer, a phosphate buffer, and mixtures thereof, and wherein the dried glucagon has a pH memory that is from about 2.0 to about 3.0; and an aprotic polar solvent selected from the group consisting of dimethylsulfoxide (DMSO), ethyl acetate, n-methyl pyrrolidone (NMP), and mixtures thereof; wherein the moisture content of the formulation is less than 5%, and wherein the dried glucagon maintains the pH memory of about 2.0 to about 3.0 when the dried glucagon is reconstituted in the aprotic polar solvent.

In still other particular embodiments, the present invention provides a stable glucagon formulation, the glucagon formulation consisting essentially of: a glucagon peptide or salt thereof (e.g., glucagon acetate), wherein the glucagon has been dried in a non-volatile buffer selected from a glycine buffer, a citrate buffer, a phosphate buffer, and mixtures thereof, and wherein the dried glucagon has a pH memory that is from about 2.0 to about 3.0; and a mixture of an aprotic polar solvent and a co-solvent that depresses the freezing point of the formulation, wherein the aprotic polar solvent is selected from the group consisting of dimethylsulfoxide (DMSO), ethyl acetate, n-methyl pyrrolidone (NMP), and mixtures thereof and wherein the co-solvent is selected from ethanol, propylene glycol, glycerol, and mixtures thereof; wherein the moisture content of the formulation is less than 5%, and wherein the dried glucagon maintains the pH memory of about 2.0 to about 3.0 when the dried glucagon is reconstituted in the aprotic polar solvent.

In other particular embodiments, the present invention provides a stable glucagon formulation, the glucagon formulation consisting essentially of: a glucagon peptide or salt thereof (e.g., glucagon acetate), wherein the glucagon has been dried in a mixture of a non-volatile buffer and a stabilizing excipient, wherein the non-volatile buffer is selected from a glycine buffer, a citrate buffer, a phosphate buffer, and mixtures thereof, and the stabilizing excipient is selected from sugars (e.g., trehalose), starches (e.g., hydroxyethyl starch (HES)), and mixtures thereof, and wherein the dried glucagon has a pH memory that is from about 2.0 to about 3.0; and an aprotic polar solvent selected from the group consisting of dimethylsulfoxide (DMSO), ethyl acetate, n-methyl pyrrolidone (NMP), and mixtures thereof; wherein the moisture content of the formulation is less than 5%, and wherein the dried glucagon maintains the pH memory of about 2.0 to about 3.0 when the dried glucagon is reconstituted in the aprotic polar solvent.

In still other particular embodiments, the present invention provides a stable formulation comprising: insulin, wherein the insulin has been dried in a first non-volatile buffer selected from a glycine buffer, a citrate buffer, a phosphate buffer, and mixtures thereof, and wherein the dried insulin has a first pH memory that is about equal to the pH of the insulin in the first non-volatile buffer, wherein the first pH memory is from about 1.5 to about 2.5, or from about 6.0 to about 8.0; pramlintide, wherein the pramlintide has been dried in a second non-volatile buffer selected from a glycine buffer, a citrate buffer, a phosphate buffer, and mixtures thereof, and wherein the dried pramlintide has a second pH memory that is about equal to the pH of the pramlintide in the second non-volatile buffer, wherein the second pH memory is from about 3.0 to about 5.0, or from about 4.0 to about 6.0; and an aprotic polar solvent selected from dimethylsulfoxide (DMSO), n-methyl pyrrolidone (NMP), ethyl acetate, and mixtures thereof; wherein the moisture content of the formulation is less than 1%, wherein the dried insulin maintains the first pH memory that is about equal to the pH of the insulin in the first non-volatile buffer when the dried insulin is reconstituted in the aprotic polar solvent, and wherein the dried pramlintide maintains the second pH memory that is about equal to the pH of the pramlintide in the second non-volatile buffer when the dried pramlintide is reconstituted in the aprotic polar solvent. In some embodiments, the insulin and pramlintide formulation further comprises a co-solvent that depresses the freezing point of the formulation, wherein the co-solvent is selected from ethanol, propylene glycol, glycerol, and mixtures thereof. In some embodiments, one or both of the insulin in the first non-volatile buffer and the pramlintide in the second non-volatile buffer further comprises a stabilizing excipient selected from sugars, starches, and mixtures thereof. In some embodiments, the first non-volatile buffer and the second non-volatile buffer are the same. In some embodiments, the first non-volatile buffer and the second non-volatile buffer are different. In some embodiments, each of the insulin and pramlintide is present in the formulation in an amount ranging from about 1 mg/mL to about 50 mg/mL. In some embodiments, the first pH memory is from about 1.5 to about 2.5. In some embodiments, the first pH memory is from about 6.0 to about 8.0. In some embodiments, the second pH memory is from about 3.0 to about 5.0. In some embodiments, the second pH memory is from about 4.0 to about 6.0. In some embodiments, the first pH memory is from about 1.5 to about 2.5 and the second pH memory is from about 3.0 to about 5.0.

IV. Methods of Making Stable Peptide Formulations

In yet another aspect, the present invention provides a process for making a stable formulation for parenteral injection. In some embodiments, the process comprises: drying a peptide and a non-volatile buffer to a dry peptide powder; and reconstituting the dried peptide powder with an aprotic polar solvent, thereby making the stable formulation, wherein the moisture content of the stable formulation is less than 5%. In some embodiments, the dried peptide powder has a pH memory that is about equal to the pH of the peptide in the non-volatile buffer, and the dried peptide powder maintains the pH memory that is about equal to the pH of the peptide in the non-volatile buffer when the dried peptide powder is reconstituted in the aprotic polar solvent.

The process for making stable peptide formulations can be used to formulate any peptide that has limited or poor stability or solubility in an aqueous environment. Peptides (or salts thereof) suitable for use in the formulations of the present invention include, but are not limited to, glucagon, insulin, leuprolide, an luteinizing-hormone-releasing hormone (LHRH) agonists, pramlintide, parathyroid hormone (PTH), amylin, botulinum toxin, a conotoxin, hematide, an amyloid peptide, cholecystikinin, gastric inhibitory peptide, an insulin-like growth factor, growth hormone releasing factor, anti-microbial factor, glatiramer, glucagon-like peptide-1 (GLP-1), a GLP-1 agonist, exenatide, and analogs thereof. In a preferred embodiment, the peptide is glucagon or a glucagon analog or peptidomimetic. In another embodiment, the peptide is parathyroid hormone. In yet another embodiment, the peptide is leuprolide. In still another embodiment, the peptide is glatiramer.

In some embodiments, two, three, four or more peptides are formulated into a stable formulation. In embodiments where two or more peptides are formulated into the stable formulation, each peptide is separately dried with a non-volatile buffer to a dry peptide powder, and each dried peptide powder has a pH memory that is about equal to the pH of the peptide in the non-volatile buffer (i.e., the first peptide has a first pH memory that is about equal to the pH of the first peptide in the first non-volatile buffer, and the second peptide has a second pH memory that is about equal to the pH of the second peptide in the second non-volatile buffer). The two or more dried peptide powders are reconstituted with an aprotic polar solvent, thereby making the stable formulation, wherein the moisture content of the stable formulation is less than 5%, and wherein each dried peptide powder maintains the pH memory that is about equal to the pH of the peptide in the non-volatile buffer when the dried peptide powder is reconstituted in the aprotic polar solvent (i.e., the first dried peptide maintains the first pH memory when the first dried peptide is reconstituted in the aprotic polar solvent, and the second dried peptide maintains the second pH memory when the second dried peptide is reconstituted in the aprotic polar solvent).

In the process for making stable peptide formulations, suitable non-volatile buffers include, for example, glycine buffers, citrate buffers, phosphate buffers, and mixtures thereof. In some embodiments, the non-volatile buffer is a glycine buffer or a citrate buffer. In some embodiments, the non-volatile buffer is a mixture of a citrate buffer and a phosphate buffer. In some embodiments, the peptide is mixed with both the non-volatile buffer and a stabilizing excipient (such as a sugar, a starch, or mixtures thereof) and then dried to a dried peptide powder. In other embodiments, the stabilizing excipient (such as a sugar, a starch, a sugar alcohol, or mixtures thereof) is added to the reconstituted peptide in the aprotic polar solvent. In some embodiments, the stabilizing excipient is present in the formulation in an amount ranging from about 1% (w/v) to about 60% (w/v), e.g., about 1%, about 5%, about 10%, about 15%, about 20%, about 25%, about 30%, about 35%, about 40%, about 45%, about 50%, about 55%, or about 60% (w/v). In some embodiments, the stabilizing excipient is trehalose. In some embodiments, the stabilizing excipient is HES. In some embodiments, the stabilizing excipient is a mixture of trehalose and HES.

As explained above, when the peptide is mixed with the non-volatile buffer, the non-volatile buffer is selected such that the peptide has a pH of maximal stability/minimal degradation in the aqueous environment. Once dried, the peptide will have a pH memory of maximal stability/minimal degradation and will retain that pH memory when dissolved in or reconstituted in the aprotic polar solvent. As such, in one embodiment, the pH of the non-volatile buffer is such that the dried peptide powder has a pH memory of about 2 to about 3. In another embodiment, the pH of the non-volatile buffer is such that the dried peptide powder has a pH memory of about 4 to about 6. In yet another embodiment, the pH of the non-volatile buffer is such that the dried peptide powder has a pH memory of about 4 to about 5. In yet another embodiment, the pH of the non-volatile buffer is such that the dried peptide powder has a pH memory of about 6 to about 8.

Once the peptide and the non-volatile buffer (and optionally other components, such as a stabilizing excipient, that are added to the peptide and the non-volatile buffer before drying) are dried to a powder, the dried peptide powder is dissolved or reconstituted in an aprotic polar solvent as described herein (e.g., dimethylsulfoxide (DMSO), n-methyl pyrrolidone (NMP), ethyl acetate, and mixtures thereof). In some embodiments, the aprotic polar solvent is dimethylsulfoxide (DMSO). In other embodiments, the aprotic polar solvent is n-methyl pyrrolidone (NMP).

In some embodiments, the step of reconstituting the dried peptide powder comprises diluting or reconstituting the dried peptide with a mixture comprising an aprotic polar solvent and a co-solvent that depresses the freezing point of the formulation. In some embodiments, the co-solvent is selected from ethanol, propylene glycol, glycerol, and mixtures thereof. In some embodiments, the co-solvent is present in the formulation in an amount ranging from about 10% (w/v) to about 50% (w/v), e.g., about 10%, about 15%, about 20%, about 25%, about 30%, about 35%, about 40%, about 45%, or about 50% (w/v).

The formulations of the present invention have very little residual moisture and, thus, the peptides in such formulations remain stable over extended periods of time. In preferred embodiments, the moisture content of the stable formulation that is made by the process of the present invention is less than 4%, less than 3%, less than 2%, less than 1%, less than 0.5%, less than 0.4%, less than 0.3%, less than 0.25%, less than 0.2%, less than 0.15%, less than 0.1%, less than 0.075%, less than 0.05%, less than 0.025%, or less than 0.01%.

In the foregoing process, drying of the peptide compound with the non-volatile buffer (and optionally the stabilizing excipient) is carried out using spray-drying techniques, freeze-drying techniques or lyophilization techniques. Spray-drying techniques are well known to those skilled in the art. Spray-drying includes the steps of atomization of a solution containing one or more solid (e.g., therapeutic agent) via a nozzle spinning disk, or other device, followed by evaporation of the solvent from the droplets. The nature of the powder that results is the function of several variables including the initial solute concentration, size distribution of droplets produced and the rate of solute removal. The particles produced may comprise aggregates of primary particles which consist of crystals and/or amorphous solids depending on the rate and conditions of solvent removal.

A spray-drying process for preparing ultra-fine powders of biological macromolecules such as proteins, oligopeptides, high molecular weight polysaccharides, and nucleic acids is described in, for example, U.S. Pat. No. 6,051,256. Freeze-drying procedures are well known in the art, and are described, for example, in U.S. Pat. No. 4,608,764 and U.S. Pat. No. 4,848,094. Spray-freeze-drying processes are described, e.g., in U.S. Pat. No. 5,208,998. Other spray-drying techniques are described, for example, in U.S. Pat. Nos. 6,253,463; 6,001,336; 5,260,306; and PCT International Publication Nos. WO 91/16882 and WO 96/09814.

Lyophilization techniques are well known to those skilled in the art. Lyophilization is a dehydration technique that takes place while a product is in a frozen state (ice sublimation under a vacuum) and under a vacuum (drying by gentle heating). These conditions stabilize the product, and minimize oxidation and other degradative processes. The conditions of freeze drying permit running the process at low temperatures, therefore, thermally labile products can be preserved. Steps in freeze drying include pretreatment, freezing, primary drying and secondary drying. Pretreatment includes any method of treating the product prior to freezing. This may include concentrating the product, formulation revision (i.e., addition of components to increase stability and/or improve processing), decreasing a high vapor pressure solvent or increasing the surface area. Methods of pretreatment include: freeze concentration, solution phase concentration, and formulating specifically to preserve product appearance or to provide lyoprotection for reactive products, and are described, e.g., in U.S. Pat. No. 6,199,297. "Standard" lyophilization conditions, are described, e.g., in U.S. Pat. No. 5,031,336, and in "Freeze Drying of Pharmaceuticals" (DeLuca, Patrick P., J. Vac. Sci. Technol., Vol. 14, No. 1, January/February 1977); and "The Lyophilization of Pharmaceuticals: A Literature Review" (Williams, N. A., and G. P. Polli, Journal of Parenteral Science and Technology, Vol. 38, No. 2, March/April 1984).

In certain preferred embodiments, the lyophilization cycle is partially performed above the glass transition temperature (Tg) of the therapeutic agent formulation to induce a collapse of the mass to form a dense cake containing residue moisture. In other embodiments, the lyophilization cycle is carried out below the glass transition temperature in order to avoid a collapse in order to achieve a complete drying of the particles.

V. Therapeutic Methods

In one particular aspect, and as already described above, the compositions of the present invention can be used to treat severe cases of hypoglycemia (e.g., wherein a human patient has a blood glucose level ranging from less than 50 mg/dL, 0 to 50 mg/dL, 0 to 40 mg/dL, 0 to 30 mg/dL, 0 to 20 mg/dL, 0 to 10 mg/dL, 10 to 50 mg/dL, 10 to 40 mg/dL. 10 to 30 mg/dL or 10 to 20 mg/dL or at or around 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 mg/dL, or any range therein). Upon administration, the human patient's blood glucose level can be increased into a more acceptable range of greater than 50 mg/dL to 180 mg/dL (e.g., 51, 52, 53, 54, 55, 56, 57, 58, 59, 60, 61, 62, 63, 64, 65, 66, 67, 68, 69, 70, 80, 90, 100, 110, 120, 130, 140, 150, 160, 170, or 180 mg/dL, or any range therein) within 1 to 20 minutes (e.g., 1, 2, 3, 4, 5, 6, 7, 8, 9, 10, 11, 12, 13, 14, 15, 16, 17, 18, 19, or 20 minutes, or any range therein) after administration.

In another aspect, the present invention provides methods of treating diseases or conditions by administering to a subject a stable formulation as described herein in an amount effective to treat, alleviate or prevent the disease, condition or disorder. In some embodiments, the disease, condition, or disorder to be treated with a stable formulation of the present invention is a diabetic condition. Examples of diabetic conditions include, but are not limited to, type 1 diabetes, type 2 diabetes, gestational diabetes, pre-diabetes, hyperglycemia, hypoglycemia, and metabolic syndrome. In some embodiments, the disease, condition, or disorder is hypoglycemia. In some embodiments, the disease, condition, or disorder is diabetes.

In some embodiments, a therapeutic method of the present invention comprises treating hypoglycemia by administering to a subject having hypoglycemia a stable formulation as described herein in an amount effective to treat the hypoglycemia. In some embodiments, the subject is administered a stable formulation comprising glucagon.

In some embodiments, a therapeutic method of the present invention comprises treating diabetes by administering to a subject having diabetes a stable formulation as described herein in an amount effective to treat the diabetes. In some embodiments, the subject is administered a stable formulation comprising insulin. In some embodiments, the subject is administered a stable formulation comprising pramlintide. In some embodiments, the subject is administered a stable formulation comprising insulin and pramlintide. In some embodiments, the subject is administered a stable formulation comprising exenatide. In some embodiments, the subject is administered a stable formulation comprising glucagon and exenatide.

Administered dosages for the peptide drugs as described herein for treating a disease, condition, disorder (e.g., a diabetic condition, e.g., hypoglycemia or diabetes) are in accordance with dosages and scheduling regimens practiced by those of skill in the art. General guidance for appropriate dosages of all pharmacological agents used in the present methods is provided in Goodman and Gilman's The Pharmacological Basis of Therapeutics, 11 th Edition, 2006, supra, and in a Physicians' Desk Reference (PDR), for example, in the 65th (2011) or 66th (2012) Eds., PDR Network, LLC, each of which is hereby incorporated herein by reference. The appropriate dosage of a peptide drug for treating a disease, condition, or disorder as described herein will vary according to several factors, including the formulation of the composition, patient response, the severity of the condition, the subject's weight, and the judgment of the prescribing physician. Effective doses of the described formulations deliver a medically effective amount of a peptide drug. The dosage can be increased or decreased over time, as required by an individual patient.

Determination of an effective amount or dose is well within the capability of those skilled in the art, especially in light of the detailed disclosure provided herein. Generally, the formulations to deliver these doses may contain one, two, three, four, or more peptides or peptide analogs (collectively "peptide," unless peptide analogs are expressly excluded), wherein each peptide is present at a concentration from about 0.1 mg/mL up to the solubility limit of the peptide in the formulation. This concentration is preferably from about 1 mg/mL to about 100 mg/mL, e.g., about 1 mg/mL, about 5 mg/mL, about 10 mg/mL, about 15 mg/mL, about 20 mg/mL, about 25 mg/mL, about 30 mg/mL, about 35 mg/mL, about 40 mg/mL, about 45 mg/mL, about 50 mg/mL, about 55 mg/mL, about 60 mg/mL, about 65 mg/mL, about 70 mg/mL, about 75 mg/mL, about 80 mg/mL, about 85 mg/mL, about 90 mg/mL, about 95 mg/mL, or about 100 mg/mL.

The formulations of the present invention may be for subcutaneous, intradermal, or intramuscular administration (e.g., by injection or by infusion). In some embodiments, the formulation is administered subcutaneously.

The formulations of the present disclosure are administered by infusion or by injection using any suitable device. For example, a formulation of the present invention may be placed into a syringe, a pen injection device, an auto-injector device, or a pump device. In some embodiments, the injection device is a multi-dose injector pump device or a multi-dose auto-injector device. The formulation is presented in the device in such a fashion that the formulation is readily able to flow out of the needle upon actuation of an injection device, such as an auto-injector, in order to deliver the peptide drugs. Suitable pen/autoinjector devices include, but are not limited to, those pen/autoinjection devices manufactured by Becton-Dickenson, Swedish Healthcare Limited (SHL Group), YpsoMed Ag, and the like. Suitable pump devices include, but are not limited to, those pump devices manufactured by Tandem Diabetes Care, Inc., Delsys Pharmaceuticals and the like.

In some embodiments, the formulations of the present invention are provided ready for administration in a vial, a cartridge, or a pre-filled syringe.

In another aspect, the present invention provides for the use of a stable formulation as described herein for the formulation of a medicament for the treatment of any disease, condition, or disorder that may be treated with the peptide of the formulation. In some embodiments, the stable formulation is used for formulating a medicament for the treatment of a diabetic condition, e.g., type 1 diabetes, type 2 diabetes, gestational diabetes, pre-diabetes, hyperglycemia, hypoglycemia, or metabolic syndrome.

In some embodiments, the stable formulation is used for formulating a medicament for the treatment of hypoglycemia. In some embodiments, the stable formulation comprises glucagon or a salt thereof (e.g., glucagon acetate). In some embodiments, the stable formulation comprises glucagon and exenatide.

In some embodiments, the stable formulation is used for formulating a medicament for the treatment of diabetes. In some embodiments, the stable formulation comprises insulin. In some embodiments, the stable formulation comprises exenatide. In some embodiments, the stable formulation comprises pramlintide. In some embodiments, the stable formulation comprises insulin and pramlintide.

VI. Kits

In another aspect, the present invention kits for treating a disease, condition or disorder as described herein. In some embodiments, the kit comprises: a stable formulation comprising one, two, three, four or more peptides or salts thereof, wherein the peptide(s) has been dried in a non-volatile buffer, and wherein the dried peptide(s) has a pH memory that is about equal to the pH of the peptide(s) in the non-volatile buffer; and an aprotic polar solvent; wherein the moisture content of the formulation is less than 5%, and wherein the dried peptide(s) maintains the pH memory that is about equal to the pH of the peptide(s) in the non-volatile buffer when the dried peptide(s) is reconstituted in the aprotic polar solvent; and a syringe for administration of the stable formulation to the subject.

In some embodiments, the kit comprises a stable glucagon formulation as described herein for use in treating hypoglycemia in a subject. In some embodiments, the kit comprises a glucagon formulation comprising: glucagon or a salt thereof (e.g., glucagon acetate), wherein the glucagon has been dried in a non-volatile buffer, and wherein the dried glucagon has a pH memory that is about equal to the pH of the glucagon in the non-volatile buffer selected from a glycine buffer, a citrate buffer, a phosphate buffer, and mixtures thereof, wherein the pH memory of the dried glucagon is from about 2.0 to about 3.0; and an aprotic polar solvent selected from dimethylsulfoxide (DMSO), n-methyl pyrrolidone (NMP), ethyl acetate, and mixtures thereof; wherein the moisture content of the formulation is less than 1%, and wherein the dried glucagon maintains the pH memory that is about equal to the pH of the glucagon in the non-volatile buffer when the dried glucagon is reconstituted in the aprotic polar solvent. In some embodiments, the glucagon formulation further comprises a co-solvent that depresses the freezing point of the formulation, wherein the co-solvent is selected from ethanol, propylene glycol, glycerol, and mixtures thereof. In some embodiments, the glucagon formulation further comprises a stabilizing excipient selected from sugars, starches, and mixtures thereof. In some embodiments, the glucagon is present in the formulation in an amount ranging from about 1 mg/mL to about 50 mg/mL.

In some embodiments, the kit comprises a stable insulin and pramlintide formulation as described herein for use in treating diabetes in a subject. In some embodiments, the kit comprises an insulin and pramlintide formulation comprising: insulin, wherein the insulin has been dried in a first non-volatile buffer selected from a glycine buffer, a citrate buffer, a phosphate buffer, and mixtures thereof, and wherein the dried insulin has a first pH memory that is about equal to the pH of the insulin in the first non-volatile buffer, wherein the first pH memory is from about 1.5 to about 2.5 or from about 6.0 to about 8.0; pramlintide, wherein the pramlintide has been dried in a second non-volatile buffer selected from a glycine buffer, a citrate buffer, a phosphate buffer, and mixtures thereof, and wherein the dried pramlintide has a second pH memory that is about equal to the pH of the pramlintide in the second non-volatile buffer, wherein the second pH memory is from about 3.0 to about 5.0 or from about 4.0 to about 6.0; and an aprotic polar solvent selected from dimethylsulfoxide (DMSO), n-methyl pyrrolidone (NMP), ethyl acetate, and mixtures thereof; wherein the moisture content of the formulation is less than 1%, wherein the dried insulin maintains the first pH memory that is about equal to the pH of the insulin in the first non-volatile buffer when the dried insulin is reconstituted in the aprotic polar solvent, and wherein the dried pramlintide maintains the second pH memory that is about equal to the pH of the pramlintide in the second non-volatile buffer when the dried pramlintide is reconstituted in the aprotic polar solvent. In some embodiments, the insulin and pramlintide formulation further comprises a co-solvent that depresses the freezing point of the formulation, wherein the co-solvent is selected from ethanol, propylene glycol, glycerol, and mixtures thereof. In some embodiments, one or both of the insulin in the first non-volatile buffer and the pramlintide in the second non-volatile buffer further comprises a stabilizing excipient selected from sugars, starches, and mixtures thereof. In some embodiments, the first non-volatile buffer and the second non-volatile buffer are the same. In some embodiments, the first non-volatile buffer and the second non-volatile buffer are different. In some embodiments, each of the insulin and pramlintide is present in the formulation in an amount ranging from about 1 mg/mL to about 50 mg/mL. In some embodiments, the first pH memory is from about 1.5 to about 2.5. In some embodiments, the first pH memory is from about 6.0 to about 8.0. In some embodiments, the second pH memory is from about 3.0 to about 5.0. In some embodiments, the second pH memory is from about 4.0 to about 6.0. In some embodiments, the first pH memory is from about 1.5 to about 2.5 and the second pH memory is from about 3.0 to about 5.0.

In some embodiments, the kit comprises a syringe that is part of a pen injection device, an auto-injector device or a pump. In some embodiment, the syringe is prefilled with the stable formulation. In some embodiments, the kit further comprises instructions, wherein the instructions direct the administration of the stable formulation to treat the subject in need thereof (e.g., the subject having hypoglycemia or diabetes).

EXAMPLES

The present invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

Example 1

Preparation of Glucagon Solutions for Use in Freeze-Drying

Various solutions were prepared to contain glucagon at a concentration of 10 mg/mL. The solutions contained, alternatively, glycine, citrate or phosphate at 5 mM, generally providing a buffer establishing a pH of 3. The solution also contained a sugar, alone or in combination, in amounts equal to the w/v amount of glucagon (1:1) or at 200% (2:1) of the amount of glucagon. The sugars were trehalose, HES, and .beta.-cyclodextrin (β-CD). Some solutions also contained Tween-20 at 0.10% w/v as a surfactant. The various formulations were mixed to substantial homogeneity in amounts as described in Table 1 below.

TABLE 1

Glucagon Mixtures for Subsequent Lyophilization

| Formulation # | Glucagon (mg/ml) | Glycine Buffer (mM) | Citrate Buffer (mM) | Phosphate Buffer (mM) | Trehalose (mg/ml) | HES (mg/ml) | β-CD (mg/ml) | Tween-20 (mg/ml) |
|---|---|---|---|---|---|---|---|---|
| 1 | 5 | 5 | 0 | 0 | 0 | 0 | 0 | 0 |
| 2 | 5 | 5 | 0 | 0 | 0 | 0 | 0 | 0.01 |
| 3 | 5 | 5 | 0 | 0 | 10 | 0 | 0 | 0 |
| 4 | 5 | 5 | 0 | 0 | 0 | 10 | 0 | 0 |
| 5 | 5 | 5 | 0 | 0 | 5 | 5 | 0 | 0 |
| 6 | 5 | 5 | 0 | 0 | 0 | 0 | 10 | 0 |
| 7 | 5 | 0 | 5 | 0 | 0 | 0 | 0 | 0 |
| 8 | 5 | 0 | 5 | 0 | 0 | 0 | 0 | 0.01 |
| 9 | 5 | 0 | 5 | 0 | 10 | 0 | 0 | 0 |
| 10 | 5 | 0 | 5 | 0 | 0 | 10 | 0 | 0 |
| 11 | 5 | 0 | 5 | 0 | 5 | 5 | 0 | 0 |
| 12 | 5 | 0 | 5 | 0 | 0 | 0 | 10 | 0 |
| 13 | 5 | 0 | 0 | 5 | 0 | 0 | 0 | 0 |
| 14 | 5 | 0 | 0 | 5 | 0 | 0 | 0 | 0.01 |
| 15 | 5 | 0 | 0 | 5 | 10 | 0 | 0 | 0 |
| 16 | 5 | 0 | 0 | 5 | 0 | 10 | 0 | 0 |
| 17 | 5 | 0 | 0 | 5 | 5 | 5 | 0 | 0 |
| 18 | 5 | 0 | 0 | 5 | 0 | 0 | 10 | 0 |
| 19 | 5 | 5 | 0 | 0 | 10 | 0 | 0 | 0.01 |
| 20 | 5 | 5 | 0 | 0 | 0 | 10 | 0 | 0.01 |
| 21 | 5 | 5 | 0 | 0 | 5 | 5 | 0 | 0.01 |

To prepare the mixtures, the glucagon was dissolved in the respective buffers (phosphate, citrate, and/or glycine buffers, 5 mM, pH 3.0) at 10 mg/mL. The solution was then mixed in a 1:1 (v/v) ratio with various solutes, which were prepared at twice the desired concentration using corresponding buffer, in order to obtain a final glucagon concentration of 5 mg/mL and the final desired solute concentration. The solutions were then filtered through 0.2 μm Millipore PES membrane to remove insoluble materials. The sample preparations were conducted in a 4° C. cold room. The glucagon concentration and the purity were determined by RP- and Size-Exclusion (SE)-HPLC.

Example 2

Preparation of Dry Glucagon Powder by Freeze-Drying

The above formulations of Table 1 were pipetted (0.3 mL) into 3-mL lyophilization vials (13-mm ID). The formulations were lyophilized in a FTS Durastop freeze-drier (Stoneridge, N.Y.). Samples were frozen at −40° C. at a ramp of 2.5° C./min and maintained for 2 hours (h) to allow sufficient freezing. The sample temperature was then increased to −5° C. at a ramp of 2° C./min and held for 2 h as an annealing step. The temperature was then decreased to 30° C. at a ramp of 1.5° C./min and the vacuum was turned on at 60 mTorr. The primary drying was set for 24 h. The temperature was gradually increased to 40° C. at a ramp of 0.5° C./min and held for additional 10 h. After drying was complete, the vials were capped under vacuum using XX stoppers from the West Pharmaceutical company (product #10123524). None of the formulations showed any evidence of cake collapse following freeze-drying. The moisture content of the final dried product was less than 1% w/w.

Example 3

Preparation of Glucagon Formulations in Aprotic Polar Solvents

Six of the dry powders made from the solutions in Table 1 were selected for formulation in polar, aprotic solvents: [0131] 1. Buffer (glycine)+trehalose (200% relative to glucagon) (formulation #3) [0132] 2. Buffer (glycine)+HES (200% relative to glucagon) (formulation #4) [0133] 3. Buffer (glycine)+trehalose (100% relative to glucagon)+ HES (100% relative to glucagon) (formulation #5) [0134] 4. Buffer (glycine)+Tween-20 (0.01% w/v)+trehalose (200% relative to glucagon) (formulation #19) [0135] 5. Buffer (glycine)+Tween-20 (0.01% w/v)+HES (200% relative to glucagon) (formulation #20) [0136] 6. Buffer (glycine)+ Tween-20 (0.01% w/v)+trehalose (100% relative to glucagon)+HES (100% relative to glucagon) (formulation #21)

Example 4

Preparation of a PTH (1-34) Solution with Low Moisture and Low Freezing Point

Solutions were prepared to contain PTH (1-34) at a concentration of 10-20 mg/mL. The solutions contained a citrate buffer establishing pH of 4-5. The solution also contained a sugar alcohol, mannitol, at a concentration of 50 mg/mL. The formulation was mixed to substantial homogeneity and freeze-dried via the drying cycle described in Example 2 to a residual moisture of less than 0.5% w/w. The dry powder is dissolved into DMSO to a concentration of 10-20 mg/mL of PTH (1-34) and 50-100 mg/mL of mannitol.

Example 5

Increase in Both Blood Glucagon and Blood Glucose Levels Following Administration of Glucagon Formulation Two nonaqueous glucagon formulations in aprotic polar solvents, based on glucagon-glycine-trehalose powders dissolved in NMP or DMSO, were tested in a rat pharmacokinetic and pharmacodynamic study and compared with an aqueous formulation. Rats were all dosed at a rate of 10 µg glucagon/rat. The nonaqueous glucagon solutions were given as 104 subcutaneous injections, as was the aqueous control solution. All formulations tested demonstrated a rapid rise in blood glucagon concentrations (see FIG. 1).

Pharmacokinetic (PK) parameters were analyzed for the four treatment groups plus the aqueous control. A noncompartmental PK analysis was performed for each rat. $C_{max}$ and $T_{max}$ were computed from observed data. Area-under-the-curve (AUC) estimates were computed without extrapolation. Data were analyzed using a five group ANOVA to compare PK parameters across groups. No significant differences in either $C_{max}$, $T_{max}$ or AUC among the three groups was observed. The relative bioavailabilities of the NMP and DMSO formulations relative to the aqueous control group were all close to 100% (76% and 92%, respectively). Thus, the nonaqueous formulations are essentially bioequivalent to the aqueous glucagon formulation based on the results of these rat PK studies.

Figure 2:
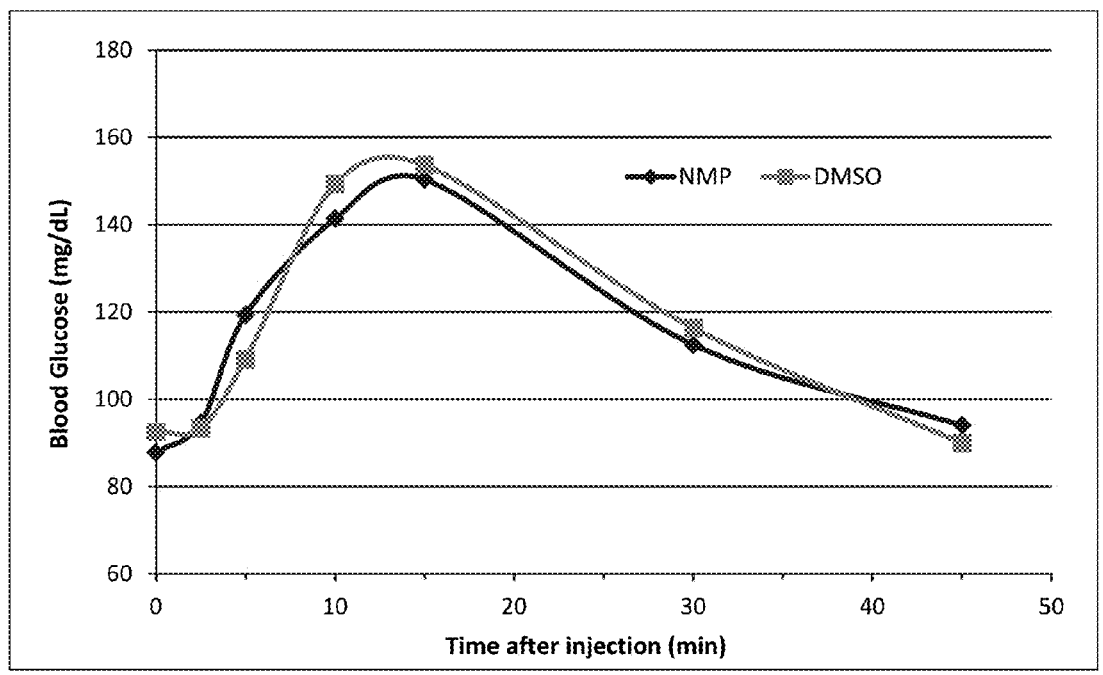
FIG. 2 illustrates blood glucose levels after injection of freeze-dried glucagon-glycine-trehalose dissolved in DMSO or NMP.

As predicted from the pharmacokinetic results, the nonaqueous glucagon formulations produced pharmacodynamic profiles essentially equivalent to an aqueous-reconstituted glucagon formulation at the same dose level (see, FIG. 2).

Example 6

Enhanced Solubility of Glucagon in Aprotic Polar Solvents Compared to Aqueous Solutions Glucagon was prepared at 1.0 mg/mL via dissolution in one of the following buffers:

1. 2 mM citric acid, pH 2.0 (titrated with concentrated HCl) ("C2.0")

2. 2 mM citric acid, pH 3.0 (titrated with concentrated HCl) ("C3.0")

Each formulation was placed in sterile 2 cc vials, at 1 mL fill volume. Samples were freeze-dried to low residual moisture and reconstituted to various nominal concentrations in DMSO, NMP, or a 50/50 DMSO/NMP co-solvent. Reconstitution concentrations ranged from 1 to 30 mg/mL. Solubility was measured by visual inspection for clarity, turbidity via $A_{630}$, and RP-HPLC.

As shown in Table 2 below, glucagon lyophilized with a citrate buffer at pH memories of 2.0 and 3.0 were readily soluble to concentrations of 30 mg/mL. The same formulations were only fully soluble in $H_2O$ at lower concentrations. For pH memory of 3.0, complete reconstitution was only achieved at 5 mg/mL in $H_2O$. Further, glucagon solubilized in $H_2O$ was only meta-stable, i.e., it only remained soluble for a few hours and then began to gel or fibrillate with rates dependent on pH and concentration, whereas glucagon solubilized in the aprotic polar solvents/co-solvents were stable indefinitely.

TABLE 2

Solubility of glucagon at pH memory of 2.0 and 3.0

| Formulation | Solvent | 1 mg/ml | 5 mg/ml | 10 mg/ml | 20 mg/ml | 30 mg/ml |
|---|---|---|---|---|---|---|
| C2.0 | $H_2O$ | 1 | 5 | 10 | 18 | 24 |
|  | DMSO | 1 | 5 | 10 | 20 | 30 |
|  | DMSO/NMP | 1 | 5 | 10 | 20 | 30 |
|  | NMP | 1 | 5 | 10 | 20 | 30 |
| C3.0 | $H_2O$ | 1 | 5 | 7 | 17 | 9 |
|  | DMSO | 1 | 5 | 10 | 20 | 30 |
|  | DMSO/NMP | 1 | 5 | 10 | 20 | 30 |
|  | NMP | 1 | 5 | 10 | 20 | 30 |

Example 7

Effect of pH on the Solubility of Glucagon in Aprotic Polar Solvents

When the data shown in Example 8 and Table 2 is viewed from a pH memory perspective, it is apparent that higher solubilities for glucagon can be achieved in the aprotic polar solvents at a lower pH memory (e.g., pH 2.0) than at a higher pH. Furthermore, although the recoveries in Table 2 indicate essentially 100% of the nominal concentration, $A_{630}$ measurements showed increasing turbidity of 30 mg/mL solutions of glucagon at pH memory of 3.0 (C3.0) in neat NMP and the DMSO/NMP co-solvent, whereas the C2.0 formulations with a pH memory of 2.0 remained essentially free of turbidity.

In another example, the effect of pH on the solubility of glucagon in aprotic polar solvents was measured for glucagon acetate dissolved in $H_2O$ at 2 mg/mL with either 2 mL glycine or 2 mM citrate buffer and pH adjusted to the desired value. Samples were freeze-dried and reconstituted to various nominal concentrations in DMSO, NMP, or a 50/50 DMSO/NMP co-solvent. Solubility was measured by visual inspection for clarity, turbidity via $A_{630}$, and RP-HPLC.

It was found that "pH memory" from lyophilization had a major effect on glucagon stability. Glucagon was soluble at up to 30 mg/mL reconstitution for "G2.5" (pH memory 2.5) lyophiles DMSO, DMSO/NMP, and NMP. Significantly reduced solubility was observed for "G3.5" (pH memory 3.5) lyophiles. G3.5 lyophiles all were cloudy and recoveries were less than complete, even at a nominal reconstitution concentration of 10 mg/mL. DMSO and the DMSO/NMP co-solvent showed about 95% recovery, whereas NMP showed only about 60% recovery.

Example 8

Effect of Buffer Species on Glucagon Stability in DMSO

Glucagon acetate was prepared at 1.0 mg/mL via dissolution in one of the following buffers:
1. 2 mM L-glycine, pH 3.0 (titrated with concentrated HCl)
2. 2 mM citric acid, pH 3.0 (titrated with concentrated HCl)

These formulations were lyophilized and reconstituted in DMSO at a nominal concentration of 5 mg/mL glucagon. Formulations were placed in stability incubators at 5° C., 25° C., and 40° C. Glucagon purity was determined with a reverse phase HPLC method.

The stability of the formulation in glycine buffer was significantly greater after 1 month of incubation at the various temperatures. Table 3 below shows the RP-HPLC purity at various times of incubation at 40° C.

TABLE 3

Effect of buffer species on the stability of glucagon in DMSO

| Formulation | Time = 0 | 1 week | 2 weeks | 4 weeks |
| --- | --- | --- | --- | --- |
| Glycine, pH 3.0 | 99.4 | 99.1 | 99.0 | 96.6 |
| Citrate, pH 3.0 | 98.6 | 97.7 | 97.3 | 92.7 |

Example 9

Effect of Moisture on Glucagon Stability in DMSO

Glucagon acetate was prepared at 1.0 mg/mL via dissolution in one of the following buffers:
1. 2 mM L-glycine, pH 3.0 (titrated with concentrated HCl)
2. 2 mM L-glycine, pH 3.0 (titrated with concentrated HCl)

These formulations were lyophilized and reconstituted in DMSO at a nominal concentration of 5 mg/mL glucagon. Additional moisture was added to the second formulation. Moisture content was measured using the Karl Fisher method. The first formulation had a moisture content of 0.13% (w/w), whereas the second formulation had a moisture content of 0.54% (w/w). Formulations were placed in stability incubators at 5° C., 25° C., and 40° C. Glucagon purity was determined with a reverse phase HPLC method.

The stability of the formulation with lower moisture was significantly greater after 1 month of incubation at the various temperatures. Table 4 below shows the RP-HPLC purity at various times of incubation at 40° C. Even at moisture contents below 1%, a significant difference in stability can be detected.

TABLE 4

Effect of residual moisture on the stability of glucagon in DMSO

| Formulation | Time = 0 | 1 week | 2 weeks | 4 weeks |
| --- | --- | --- | --- | --- |
| Lower moisture | 99.4 | 99.1 | 99.0 | 96.6 |
| Additional moisture | 99.2 | 98.9 | 98.8 | 95.6 |

Example 10

Freezing Point Depression of DMSO Solutions

Using PerkinElmer Instruments PYRIS Diamond Differential Scanning calorimetry ("DSC"), samples were cooled to −40° C. and heated to 40° C. at 8° C. per minute for screening purposes.

DMSO/NMP Blends

Various DMSO and NMP blends were tested, including:
1. 90% DMSO+10% NMP
2. 80% DMSO+20% NMP
3. 70% DMSO+30% NMP
4. 60% DMSO+40% NMP
5. 50% DMSO+50% NMP DSC scans showed that the temperature of crystallization of the solvents progressively reduced from ~−18° C. for neat DMSO to −5.7° C. for a 50% NMP/50% DMSO blend. Addition of the glucagon acetate, glycine lyophile to a glucagon concentration of 5 mg/mL resulted in an additional ~1° C. reduction in the freezing point.

DMSO/Ethyl Acetate Blends

Various DMSO and ethyl acetate blends were tested, including:
1. 80% DMSO+20% ethyl acetate ($T_c$=16° C.)
2. 70% DMSO+30% ethyl acetate
3. 60% DMSO+40% ethyl acetate ($T_c$=6.5° C.)
4. 50% DMSO+50% ethyl acetate ($T_c$=2.9° C.)
5. 40% DMSO+60% ethyl acetate ($T_c$=none observed)

DSC scans showed that the temperature of crystallization of the solvents progressively reduced from ~−18° C. for neat DMSO to 2.9° C. for a 50% NMP/50% DMSO blend. No crystallization peak was observed for a 40% DMSO/60% ethyl acetate blend. Additionally, these formulations were stored at refrigerated temperature (4° C.) for several days and observed visually for evidence of freezing. All formulations with 30% ethyl acetate or greater in the co-solvent stayed liquid and did not freeze. This is somewhat different from the $T_c$ observed in the DSC studies.

DMSO Solutions with Alcohol Co-Solvents

Various DMSO solutions to which an alcohol co-solvent (ethanol, glycerol, or propylene glycol) were added were tested, including:

1. 95% DMSO+5% alcohol
2. 90% DMSO+10% alcohol
3. 80% DMSO+20% alcohol
4. 70% DMSO+30% alcohol
5. 60% DMSO+40% alcohol
6. 50% DMSO+50% alcohol
7. 40% DMSO+60% alcohol
8. 30% DMSO+70% alcohol
9. 20% DMSO+80% alcohol
10. 10% DMSO+90% alcohol These formulations were stored at refrigerated temperature (4° C.) for several days and observed visually for evidence of freezing. All formulations with 20% alcohol co-solvent or greater stayed liquid and did not freeze. DSC scans showed the freezing point of 20% alcohol co-solvents to be 2.3° C., 0.6° C., and 3.3° C. for ethanol, glycerol, and propylene glycol, respectively.

Example 11

Freeze-Thaw Stability of Glucagon

Glucagon acetate was prepared at 1.0 mg/mL via dissolution in 2 mM L-glycine, pH 3.0 (titrated with concentrated HCl). The glucagon formulations were lyophilized and reconstituted in DMSO at a nominal concentration of 5 mg/mL glucagon. Solution samples were divided and trehalose was added to one solution to a concentration of 5%. These formulations were aliquoted into vials and placed in a stability incubator at 5° C. At 5° C., these solutions were observed to freeze. The glucagon solutions were thawed at various intervals and turbidity was determined using the absorbance at 630 nm.

Table 5 below shows the turbidity of the glucagon solutions at various times of incubation at 5° C. The solutions without trehalose showed increases in turbidity at various time points of incubation. Solutions containing trehalose, however, showed no increase in turbidity. The turbidity measurements were confirmed through visual observation. Samples frozen and incubated without trehalose were cloudy or hazy upon observation.

TABLE 5

Turbidity of glucagon solutions after incubation at 5° C.

| Formulation | Time = 0 | 1 week | 2 weeks | 4 weeks |
|---|---|---|---|---|
| No trehalose | 0.024 | 0.142 | 0.130 | 0.160 |
| 5% trehalose | 0.016 | 0.029 | 0.028 | 0.035 |

Surprisingly, use of a carbohydrate additive such as trehalose in solutions of peptides in DMSO enhances the stability of the peptide during the freeze-thawing process.

Example 12

Enhanced Thawing Rate with Trehalose

Glucagon acetate was prepared at 1.0 mg/mL via dissolution in 2 mM L-glycine, pH 3.0 (titrated with concentrated HCl) as described above for Example 13. Upon removal from storage at 5° C., samples of glucagon solutions containing trehalose were observed to thaw completely in a much shorter time than solutions without trehalose. Trehalose-containing samples were observed to thaw completely in less than 30 seconds, as contrasted with glucagon solutions without trehalose, which were typically observed to thaw completely over several minutes. The ability to quickly thaw a peptide formulation can be particularly advantageous in an emergency medical setting, in the event a solution was frozen and had to be injected rapidly.

Example 13

Effect of pH on Insulin Solubility

Insulin was dissolved in $H_2O$ at 10 mg/mL with a 10 mM phosphate/citrate-1 mM EDTA buffer at either pH 2 or pH 7. These solutions were lyophilized to dryness (>1% residual moisture) using a conservative cycle and reconstituted to various nominal concentrations in DMSO. Solubility was measured by visual inspection for clarity and turbidity via $A_{630}$.

At a pH of 2, insulin was observed to be soluble to concentrations of at least 100 mg/mL. However, at a pH memory of 7, even at the lowest concentration tested, 10 mg/mL, poor solubility of insulin was observed as cloudy or hazy solutions with increased light scattering ($A_{630}$). Some lower-concentration, e.g., 10 mg/mL, insulin solutions with a pH memory of 7 were observed to slowly dissolve to a clear solution over a period of about 24 hours.

Example 14

Effect of pH on Pramlintide Solubility

Pramlintide acetate was dissolved in $H_2O$ at 2 mg/mL with either a 10 mM citrate buffer, pH 4 or 10 mM phosphate buffer, pH 7. These solutions were lyophilized to dryness (>1% residual moisture) using a conservative cycle and reconstituted to various nominal concentrations in DMSO. Solubility was measured by visual inspection for clarity and turbidity via $A_{630}$.

At no concentration was pramlintide with a pH memory of 7 soluble in DMSO. However, a low concentration of pramlintide with a pH memory of 4 was soluble in DMSO.

Example 15

Co-Formulations of Peptides in Aprotic Polar Solvents

Preparation of co-formulations are prepared by separately drying formulations of the individual compounds from an aqueous solution that provides the optimal solubility/stability upon reconstitution into the aprotic polar solvent. Solution pH is a property that affects peptide solubility, and a dried peptide, when reconstituted into an aprotic polar solvent, will retain a "pH memory" of the aqueous formulation from which it was dried when a non-volatile buffer is used. Since aprotic polar solvents do not have exchangeable protons, the individual peptides will maintain the solubility and stability characteristics of the optimal pH memory.

Current pramlintide and insulin formulations conflict in their buffering systems, making compatibility of a mixed formulation difficult. Most insulins and insulin analogs have an isoelectric point in the range of 5-6 and are thus formulated at a pH of around 7 or at a lower pH of around 2. Pramlintide has an isoelectric point of >10.5 and is formulated at a pH of around 4 where it is optimally stable. The interaction of pramlintide and insulin formulations at different pHs and differing buffering capacities often results in precipitation of soluble insulin components or solubilization of crystalline insulin components. In vitro studies with pramlintide and short- and long-acting insulin formulations found substantial variability in insulin solubility when various quantities of insulin were mixed with fixed quantities of pramlintide.

Thus, the present invention provides a formulation whereby both a rapid-acting insulin species and an amylin analog are stable and can be administered simultaneously from a single formulation for injection or formulation. This formulation more closely mimics the natural physiological response to post-prandial rise in blood glucose than the prior art.

Examples of peptides that can be co-formulated include, but are not limited to: (1) insulin-amylin (insulin at a pH memory of about 2.0 or about 7.0, and amylin or an amylin analog (e.g., pramlintide) at a pH memory of about 4.0); and (2) glucagon-GLP-1 (glucagon at a pH memory of about 3.0 or below, and glucagon-like peptide-1 (GLP-1) or an analog thereof (e.g., exenatide) at a pH memory of about 4.0-5.0).

A co-formulation of insulin and pramlintide was prepared as follows: An insulin formulation of 100 mg/mL insulin, pH memory 2, was made as described above in Example 14. A pramlintide formulation of 1 mg/mL pramlintide, pH memory 4, was made as described above in Example 15. 5 µl of the insulin formulation was mixed with 95 ml of the pramlintide solution. The resulting solution was observed to be clear and thus created a soluble co-formulation of insulin and pramlintide with respective pH memory of 2 and 4, respectively.

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications, patents and PCT publications are incorporated herein by reference for all purposes.

Example 16

Data Concerning Treatment of Severe Hypoglycemia

This example concerns data obtained from a study ("Study CB12-5015-R-TX") performed to compare the use of a glucagon containing formulation of the present invention ("Xeris Glucogon") with that of a known glucacon formulation offered by Eli Lilly ("Lilly Glucagon"). The Xeris Glucagon formulation was prepared in a manner described in the above Examples and is characterized below in Table 6.

Pre-lyophilized bulk drug product is prepared in an aqueous solution of 1.0 mg/mL glucagon, 2 mM glycine, and 0.10% w/w trehalose, at pH 3.0 as follows:

1. Combine 0.05 g glycine, 2.34 g trehalose and 2095.5 g water-for-injection (WFI), to create a 2.0 mM glycine, 0.1% trehalose solution.
2. Measure pH and adjust to 3.0 with 1.0 N HCl if needed. If HCl added, check pH a second time.
3. Weigh ~2.10 g glucagon powder (adjusted for the peptide content per glucagon CofA as peptide content of synthetic glucagon varies, but is approximately 94%) and dissolve glucagon powder in the buffer. Mix to reach a final concentration of 1.0 mg/mL glucagon. Verify concentration with UV-Vis$_{A280}$ (AM500-54).
4. Filter solution with a Millipak 200 0.45 µm PVDF polishing filter to remove particulate.
5. Utilizing a bio-safety cabinet (BSC) fill 10.0 g aliquots into 20 mL glass vials, and stopper with single-vent lyo stoppers.
6. Place vials on a lyophilization tray, load into the BOC Edwards lyophilizer and initiate cycle. The lyophilization cycle is provided in Table 7.

The intermediate bulk drug product includes glucagon lyophiles reconstituted in trehalose/DMSO that are pooled and aseptically filtered, creating a formulation of 5.0 mg/mL glucagon, 10 mM glycine, 5.00% w/w trehalose, and 94.54% w/w DMSO, with "pH memory" 3.0. All materials used in intermediate drug product formulation steps are DMSO compatible.

1. Weigh 21.01 g trehalose and dissolve in 500 mL DMSO. Mix 4.50% trehalose in DMSO to create the non-aqueous reconstitution solution.
2. Dissolve individual glucagon lyophiles by adding reconstitution solution to each vial, with a target concentration of 5.0 mg/mL glucagon (and a final trehalose concentration of 5.00%).
3. Pool reconstituted vials into a glass filling vessel and mix.
4. Assay for UV-Vis$_{A280}$ (AM500-54) to determine if further dilution with the solvent mixture is required to achieve the target concentration.
5. If dilution with the solvent mixture is required, again assay for UV-Vis$_{A280}$.
6. Place batch in BSC and sterile filter using a Meissner 0.22 µm capsule filter with DMSO-compatible PTFE membrane.

TABLE 6

| Component | Concentration (% w/w) |
| --- | --- |
| Glucagon | 0.45 |
| Glycine | 0.01 |
| Trehalose | 5.00 |
| Dimethyl sulfoxide (DMSO) | 94.54 |
| Hydrochloric acid[1] | |
| Total: | 100.00 |

[1]Variable depending on pH adjustment required: usually ~5 mL per batch

TABLE 7

| Phase | Temperature | Rate | Time | Pressure |
| --- | --- | --- | --- | --- |
| Shelf Load | 5° C. | N/A | 1 hour | N/A |
| Freezing | 5° C. to −50° C. | 1° C./min | 45 min | N/A |

TABLE 7-continued

| Phase | Temperature | Rate | Time | Pressure |
|---|---|---|---|---|
| | −50° C. | N/A | 2 hours | N/A |
| Annealing | −50° C. to −15° C. | 1° C./min | 25 min | N/A |
| | −15° C. | N/A | 1 hour | N/A |
| Primary Drying | −15° C. | N/A | 59 hours | 100 mTorr |
| Secondary Drying | −15° C. to 25° C. | 1° C./min | 40 min | 100 mTorr |
| | 25° C. | N/A | 23* hours | 100 mTorr |
| Pre-Aeration/Stoppering | 25° C. | N/A | 17 min | 13.5 psia |
| Aeration | 25° C. | N/A | 5 min | Atmosphere |
| Storage Temp | 5° C. | N/A | 1 hour | Atmosphere |

The Lilly Glucagon (Glucagon for Injection) formulation is characterized in literature as including the following ingredients: Glucagon for Injection (rDNA origin) is a polypeptide hormone identical to human glucagon that increases blood glucose and relaxes smooth muscle of the gastrointestinal tract. Glucagon is synthesized in a special non-pathogenic laboratory strain of *Escherichia coli* bacteria that has been genetically altered by the addition of the gene for glucagon. Glucagon is available for use intravenously, intramuscularly, or subcutaneously in a kit that contains a vial of sterile glucagon and a syringe of sterile diluent. The vial contains 1 mg (1 unit) of glucagon and 49 mg of lactose. Hydrochloric acid may have been added during manufacture to adjust the pH of the glucagon. One International Unit of glucagon is equivalent to 1 mg of glucagon. The diluent syringe contains 12 mg/mL of glycerin, water for injection, and hydrochloric acid. (*Drug Information for the Health Care Professional*. 18th ed. Rockville, Md.: The United States Pharmacopeial Convention, Inc; 1998; 1:1512, which is incorporated by reference).

The pharmacokinetics and pharmacodynamics phase of Study CB12-5015-R-TX consisted of 4 groups of jugular vein-cannulated (JVC) outbred SD-HLA®(SD)CVF® (Sprague-Dawley rats from Hilltop Lab Animals, Inc.) male (n=10) and female (n=10) rats. Prior to study start, the animals were examined, weighed, and assigned randomly to any one of 4 study treatment groups. Animals were fasted overnight before dosing. The rats were injected SC with 2.5 µg Xeris Glucagon, 5 µg Xeris Glucagon, 50 µg Xeris Glucagon or with 5 µg Lilly Glucagon. Blood was collected from each animal pre-dosing (t=0 min), and 2.5., 5, 10, 15, 30, 45 and 60 min post-dose for determination of blood glucose and plasma glucagon concentrations. The overall study scheme is summarized in Table 8.

Data files containing individual measurements for treatment groups from Study CB12-5015-R-TX were obtained. Three animals (Numbers 556, 657, 805) were lost to analysis due to missing values (Table 9). Summary statistics (mean, median, minimum, maximum, standard deviation, standard error of the mean, confidence intervals) were derived from a merged glucose and glucagon concentration dataset for any one treatment group and time period post-dose.

TABLE 9

| Experimental Group | Treatment Group | gender | n |
|---|---|---|---|
| 5-8 | All | All | 77 |
| 5-8 | All | Female | 38 |
| 5-8 | All | Male | 39 |
| 5 | 2.5 µg Xeris Glucagon | All | 19 |
| 6 | 5 µg Xeris Glucagon | All | 19 |
| 7 | 50 µg Xeris Glucagon | All | 20 |
| 8 | 5 µg Lilly Glucagon | All | 19 |
| 5 | 2.5 µg Xeris Glucagon | Female | 9 |
| | | Male | 10 |
| 6 | 5 µg Xeris Glucagon | Female | 9 |
| | | Male | 10 |
| 7 | 50 µg Xeris Glucagon | Female | 10 |
| | | Male | 10 |
| 8 | 5 µg Lilly Glucagon | Female | 10 |
| | | Male | 9 |

Normality was assessed with the Anderson-Darling test and accepted if p>0.05. Data were transformed using natural logs before applying analysis of variance (ANOVA), and then the confidence intervals where back-transformed for presentation. A parametric (normal-theory) general linear model was applied to the pharmacokinetic ($AUC_{(0-\infty)}$, $C_{max}$, $t_{max}$, CL, $t_{1/2}$, dose-proportionality) and pharmacodynamic ($BG_{max}$, $TBG_{max}$, $AUC_{(0-60\ min)}$, MAE, $T_{MAE}$) parameters. The ANOVA model included study treatment group and period as factors. For PK and PD parameters, ANOVA was performed for comparison of means by group and gender. Means for any one treatment group and time period were compared using ANOVA. Differences between the treatment groups with respect to any given parameter were assessed using Bonferroni t-tests of pair-wise multiple comparisons adjusted to maintain overall levels of significance at α=0.05. Dose proportionality was assessed by simple linear regression of the dose-normalized parameters versus dose, and concluded if the slope was not significantly different from 0

TABLE 8

| | | Study Treatment | | | |
|---|---|---|---|---|---|
| Experimental Group | Animal No. (male/female) | Treatment Group | Dose | SC Injection Volume | Blood Volume |
| 5 | 501-510/ 551-560 | Xeris Glucagon | 2.5 µg | 0.5 µL | Blood samples (~0.35 mL/time point) pre-dose (time 0) and 2.5, 5, |
| 6 | 601-610/ 651-660 | Xeris Glucagon | 5 µg | 1 µL | 10, 15, 30, 45, and 60 min post-dose One drop of whole blood for glucose |
| 7 | 701-710/ 751-760 | Xeris Glucagon | 50 µg | 10 µL | level using a rodent glucometer Remainder (~0.3 mL) transferred to |
| 8 | 801-810/ 851-860 | Lilly Glucagon | 5 µg | 5 µL | EDTA-tube with 75,000 IU aprotinin. Plasma frozen at −80° C. until PK assay of glucagon concentration |

($\alpha=0.05$). Appropriate PKPD calculations were based on non-compartmental methods. All calculations were performed using SAS version 9.2 (Cary, N.C.). The level of significance for all statistical hypothesis testing was considered at $\alpha=0.05$.

Plasma Glucagon Concentrations, $C_{max}$, $t_{max}$, and $AUC_{(0-\infty)}$. Pharmacokinetic endpoints were analyzed for the Xeris Glucagon and Lilly Glucagon treatment groups. Dosing of rats with 2.5 μg Xeris Glucagon, 5 μg Xeris Glucagon, 50 μg Xeris Glucagon or with 5 μg Lilly Glucagon resulted in a rapid rise (2.5 min to 5 min post-dose) in plasma glucagon concentrations in all treatment groups from the t=0 min pre-treatment levels (FIG. 3 and Table 10).

TABLE 10

| Treatment Group | Time Post-Dose (min) | [Plasma Glucagon] (pg/ml) Mean | SEM |
|---|---|---|---|
| 2.5 μg Xeris Glucagon | 0 | 629.8 | 277.2 |
| | 2.5 | 8,071.5 | 1,339.1 |
| | 5 | 7,151.0 | 1,423.1 |
| | 10 | 3,222.9 | 598.3 |
| | 15 | 936.4 | 178.0 |
| | 30 | 492.4 | 379.5 |
| | 45 | 54.3 | 3.2 |
| | 60 | 43.0 | 3.9 |
| 5 μg Xeris Glucagon | 0 | 92.6 | 21.1 |
| | 2.5 | 10,076.7 | 1,443.6 |
| | 5 | 11,386.1 | 1,584.9 |
| | 10 | 6,365.0 | 756.5 |
| | 15 | 3,015.3 | 636.6 |
| | 30 | 542.2 | 205.0 |
| | 45 | 96.7 | 29.1 |
| | 60 | 51.4 | 7.3 |
| 50 μg Xeris Glucagon | 0 | 68.2 | 2.4 |
| | 2.5 | 35,316.6 | 7,000.1 |
| | 5 | 70,457.4 | 7,757.8 |
| | 10 | 67,914.5 | 5,619.7 |
| | 15 | 35,722.6 | 3,717.8 |
| | 30 | 12,375.2 | 1,408.5 |
| | 45 | 3,773.9 | 522.0 |
| | 60 | 1,302.6 | 240.7 |
| 5 μg Lilly Glucagon | 0 | 64.7 | 3.3 |
| | 2.5 | 3,974.2 | 576.9 |
| | 5 | 5,860.3 | 934.5 |
| | 10 | 5,326.4 | 1,127.7 |
| | 15 | 2,236.7 | 409.4 |
| | 30 | 355.4 | 96.5 |
| | 45 | 125.8 | 25.3 |
| | 60 | 83.5 | 14.2 |

Figure 3:
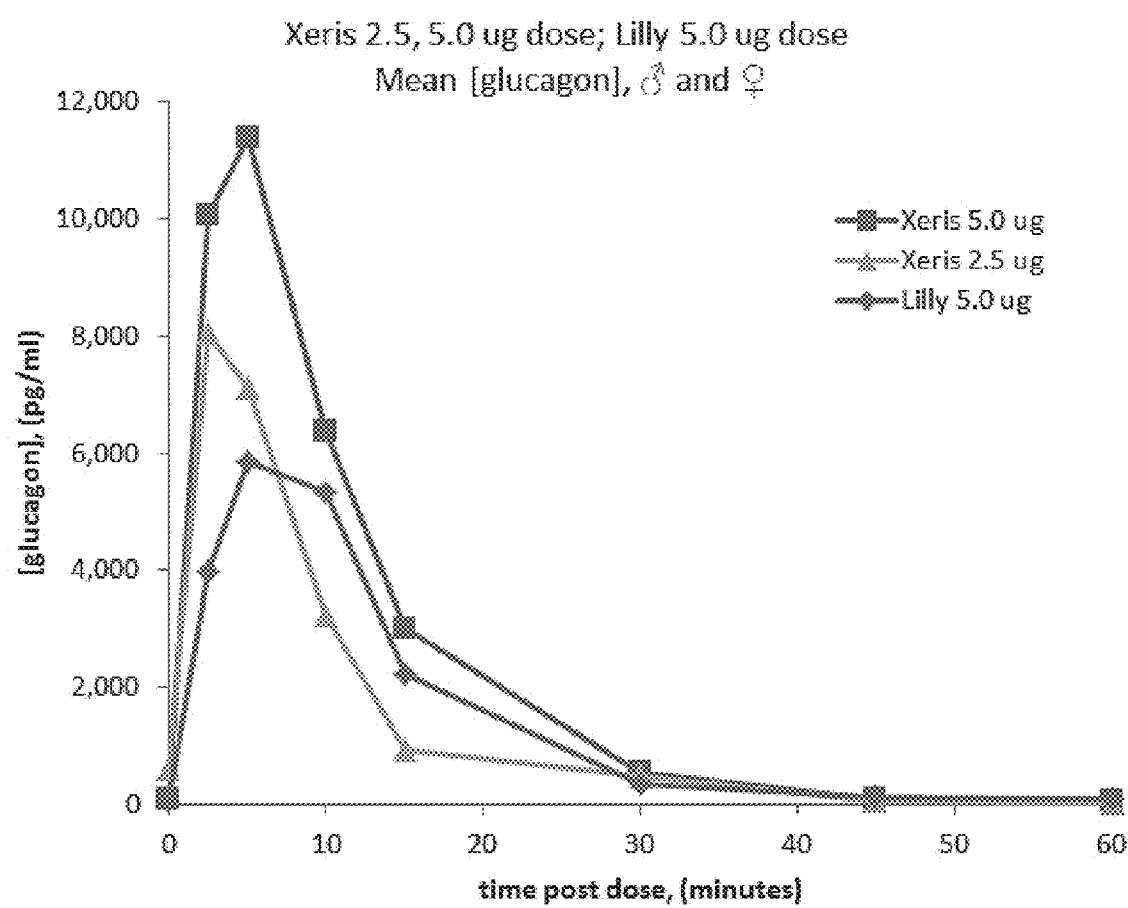
FIG. 3 compares plasma glucagon concentrations of a Xeris Glucagon and a Lilly Glucagon post administration.

The plasma glucagon concentrations of groups treated with 2.5 μg Xeris Glucagon, 5 μg Xeris Glucagon or 5 μg Lilly Glucagon were similar during the time course of the study (FIG. 3).

There was a proportional relationship (dose proportionality; Testing Ho: ($\beta=0$, p=0.3085) between the Xeris Glucagon SC injection dose and the measured plasma glucagon concentration. Whereas the mean $C_{max}$ concentrations were not significantly different by gender (p=0.3601) nor by gender within groups (p=0.3543), the $C_{max}$ from the 4 treatment groups was significantly (p<0.0001) different, with the 50 μg Xeris Glucagon treatment resulting in greater (p<0.0001) $C_{max}$ (78,640 μg/ml) than that of any other treatment group (Table 11). Subcutaneous injection with 5 μg Xeris Glucagon gave rise to significantly (p=0.0424) greater $C_{max}$ than did treatment with 5 μg Lilly Glucagon (Table 11).

TABLE 11

| | $C_{max}$ (pg/ml) | | |
|---|---|---|---|
| Treatment Group | Mean | SEM | 95% CI |
| 2.5 μg Xeris Glucagon | 8,540 | 1,376 | 4,783-9,649 |
| 5 μg Xeris Glucagon | 12,604 [a] | 2,892 | 6,696-15,033 |
| 50 μg Xeris Glucagon | 76,640 [b] | 17,584 | 60,446-88,321 |
| 5 μg Lilly Glucagon | 6,544 | 1501 | 3,703-7,472 |

[a] p = 0.0424 vs 5 μg Lilly Glucagon
[b] p < 0.0001 vs any one treatment group

A comparison of mean time of peak glucagon concentration ($t_{max}$) showed significant differences in $t_{max}$ by treatment group (p=0.0022) and by gender (p=0.0499; Table 12). The $t_{max}$ between groups treated with 2.5 μg Xeris Glucagon, 5 μg Xeris Glucagon or 5 μg Lilly Glucagon was similar (p=0.3238; Table 11). However, a single subcutaneous injection of 50 μg Xeris Glucagon resulted in a longer $t_{max}$ (7.50±0.68 min; group mean±SEM) when compared with SC injection of 2.5 μg Xeris Glucagon (5.13±1.41 min; p=0.0030) or 5 μg Xeris Glucagon (4.87±0.70 min; p=0.0114). No significant difference in $t_{max}$ was found between the 50 μg Xeris Glucagon and the 5 μg Lilly Glucagon-treated group (7.50±0.68 min vs 5.53±0.59 min, respectively; p=0.2488).

TABLE 12

| | | $t_{max}$ (min) | | |
|---|---|---|---|---|
| Treatment Group | Gender | Mean | SEM | 95% CI |
| 2.5 μg Xeris Glucagon | Male | 6.25 | 2.67 | 0.21-12.29 |
| | Female | 3.89 | 0.44 | 2.88-4.90 |
| 5 μg Xeris Glucagon | Male | 6.00 | 1.19 | 3.31-8.69 |
| | Female | 3.61 | 0.44 | 2.60-4.62 |
| 50 μg Xeris Glucagon [a] | Male | 7.50 | 0.83 | 5.61--9.39 |
| | Female | 7.50 | 1.12 | 4.97-10.03 |
| 5 μg Lilly Glucagon | Male | 6.39 | 0.94 | 4.22--8.56 |
| | Female | 4.75 | 0.69 | 3.18-6.32 |

[a] p = 0.0030 vs 2.5 μg Xeris Glucagon or 5 μg Xeris Glucagon

The $AUC_{(0-\infty)}$ of treatment groups injected SC with 2.5 μg Xeris Glucagon, 5 μg Xeris Glucagon or with 5 μg Lilly Glucagon was similar (p=0.0995; Table 13). Dosing with 50 μg Xeris Glucagon resulted in significantly greater (p<0.0001) $AUC_{(0-\infty)}$ when compared with the $AUC_{(0-\infty)}$ from any one treatment group (Table 13). The mean $AUC_{(0-\infty)}$ from the treatment groups were not significantly different by gender (p=0.4468) nor significantly different by gender within groups (p=0.1838). The $AUC_{(0-\infty)}$ was not normally distributed (p<0.0005), and the values were transformed with natural logarithms for analysis.

TABLE 13

| Treatment Group | Gender | $AUC_{(0-\infty)}$ Mean | SEM | 95% CI |
|---|---|---|---|---|
| 2.5 μg Xeris Glucagon | Male | 69,134 | 12,539 | 30,022-99,092 |
| | Female | 94,751 | 22,400 | 36,982-138,899 |
| 5 μg Xeris Glucagon | Male | 169,569 | 25,101 | 76,496-252,812 |
| | Female | 106,589 | 18,968 | 41,349-170,468 |
| 50 μg Xeris Glucagon [a] | Male | 1,206,337 | 13,0603 | 807,017-1,551,604 |
| | Female | 1,446,123 | 15,7531 | 1,077,981-1,751,179 |
| 5 μg Lilly Glucagon | Male | 107,799 | 19,271 | 52,250-157,314 |
| | Female | 66,337 | 13,536 | 37,023-86,008 |

[a] p < 0.0001 when compared with any one treatment group t½ and CL Pharmacokinetic Endpoints. Dosing with either 2.5 µg, 5 µg or 50 µg Xeris Glucagon resulted in similar t½ and clearance (CL) endpoints to administration of the 5 µg Lilly Glucagon reference drug (p=0.2432 and p=0.0622, respectively; Table 14). No significant difference in t½ was found by gender (p=0.6480) or by gender within groups (p=0.1539). Similarly, the CL did not differ between the treatment groups by gender (p=0.4468) or by gender within groups (p=0.1838; Table 14).

TABLE 14

| Treatment Group | Gender | t½ (min) | | | Clearance (mL/min) | | |
|---|---|---|---|---|---|---|---|
| | | Mean | SEM | 95% CI | Mean | SEM | 95% CI |
| 2.5 µg Xeris glucagon | Male | 13.6 | 2.8 | 6.1-9.3 | 66.55 | 22.49 | 25.23-83.27 |
| | Female | 9.2 | 1.2 | 8.0-17.2 | 49.38 | 15.58 | 18-67.6 |
| 5 µg Xeris glucagon | Male | 7.9 | 1.0 | 6.9-10.4 | 58.86 | 29.24 | 19.78-65.36 |
| | Female | 10.5 | 3.5 | 6.7-6.7 | 106.39 | 59.08 | 29.33-120.92 |
| 50 µg Xeris glucagon | Male | 8.2 | 0.6 | 5.4-13.2 | 50.33 | 10.52 | 32.23-61.96 |
| | Female | 9.4 | 0.8 | 6.5-11.4 | 38.36 | 4.34 | 28.55-46.39 |
| 5 µg Lilly glucagon | Male | 8.8 | 1.0 | 8.0-13.7 | 74.89 | 28.25 | 31.78-95.7 |
| | Female | 11.3 | 1.7 | 7.7-10.9 | 102.60 | 18.28 | 58.14-135.04 |

Blood Glucose Concentration-Time Profiles, $BG_{max}$ and $TBG_{max}$ in Rats Treated by Subcutaneous Injection of Glucagon. Blood glucose levels at baseline (t=0, pre-dosing) were normally distributed (p=0.3185) across all groups (n=77 rats) in the study. There were no differences in the pre-treatment blood glucose concentrations in the study groups (treatment, p=0.8647; gender, p=0.0820; gender-group Interaction, p=0.3426; Table 15).

A single SC injection of glucagon resulted in marked elevations in blood glucose concentrations in all treated male (144±2 mg/dL, mean±SEM; 95% Confidence Interval, 140 mg/dL to 147 mg/dL) and female (140±2 mg/dL; 95% Confidence Interval, 136 mg/dL to 143 mg/dL) rats from the t=0 pre-dose levels (mean 112 mg/dL for male rats; 106 mg/dL for female rats; Table 15.

TABLE 15

| | | | Glucose (mg/dL) | | |
|---|---|---|---|---|---|
| Treatment Group | Gender | n | Mean | SD | 95% CI |
| All | All | 77 | 109 | 15 | 106-113 |
| All | Female | 38 | 106 | 16 | 101-111 |
| All | Male | 39 | 112 | 14 | 108-117 |
| 2.5 µg Xeris Glucagon | All | 19 | 111 | 11 | 106-116 |
| 5 µg Xeris Glucagon | All | 19 | 111 | 15 | 104-118 |
| 50 µg Xeris Glucagon | All | 20 | 108 | 14 | 101-114 |
| 5 µg Lilly Glucagon | All | 19 | 108 | 19 | 99-117 |
| 2.5 µg Xeris Glucagon | Female | 9 | 105 | 8 | 98-111 |
| | Male | 10 | 117 | 9 | 110-123 |
| 5 µg Xeris Glucagon | Female | 9 | 110 | 10 | 102-117 |
| | Male | 10 | 112 | 19 | 98-126 |
| 50 µg Xeris Glucagon | Female | 10 | 102 | 17 | 90-114 |
| | Male | 10 | 114 | 8 | 108-120 |
| 5 µg Lilly Glucagon | Female | 10 | 109 | 23 | 92-126 |
| | Male | 9 | 107 | 14 | 96-118 |

Figure 4:
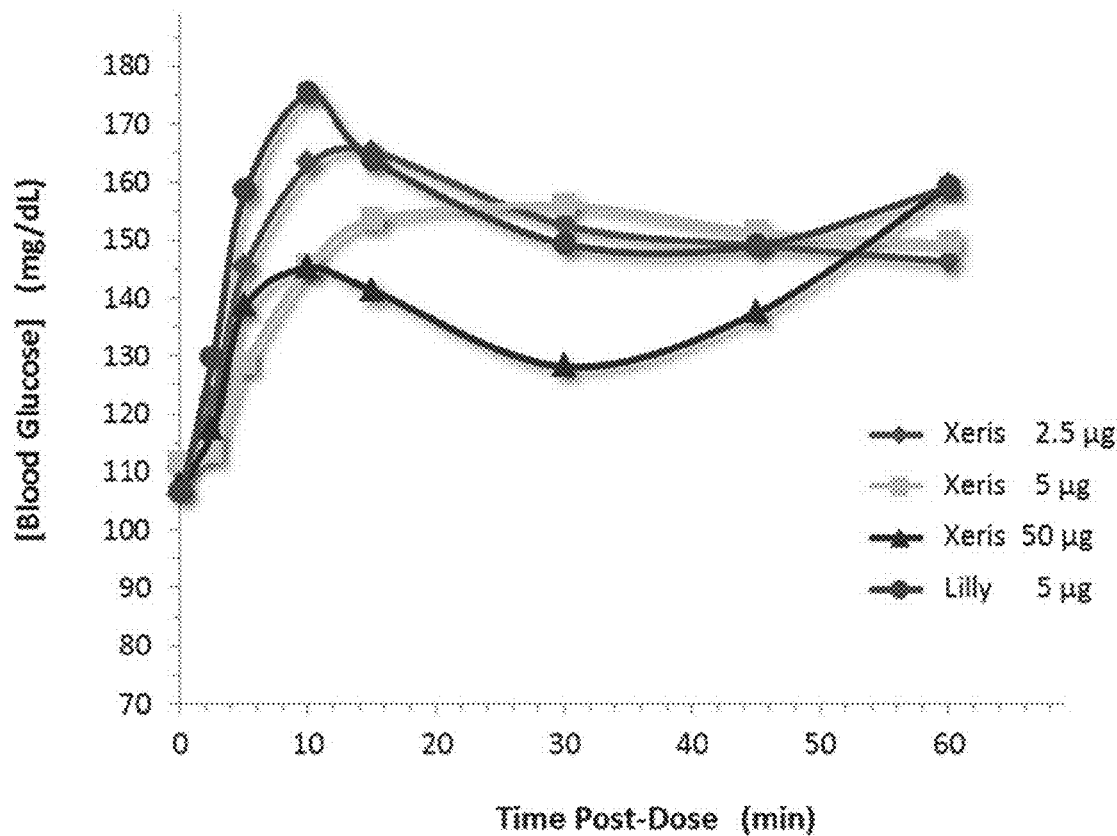
FIG. 4 compares blood glucose level measurements after administration of a Xeris Glucagon and a Lilly Glucagon.
Figure 5:
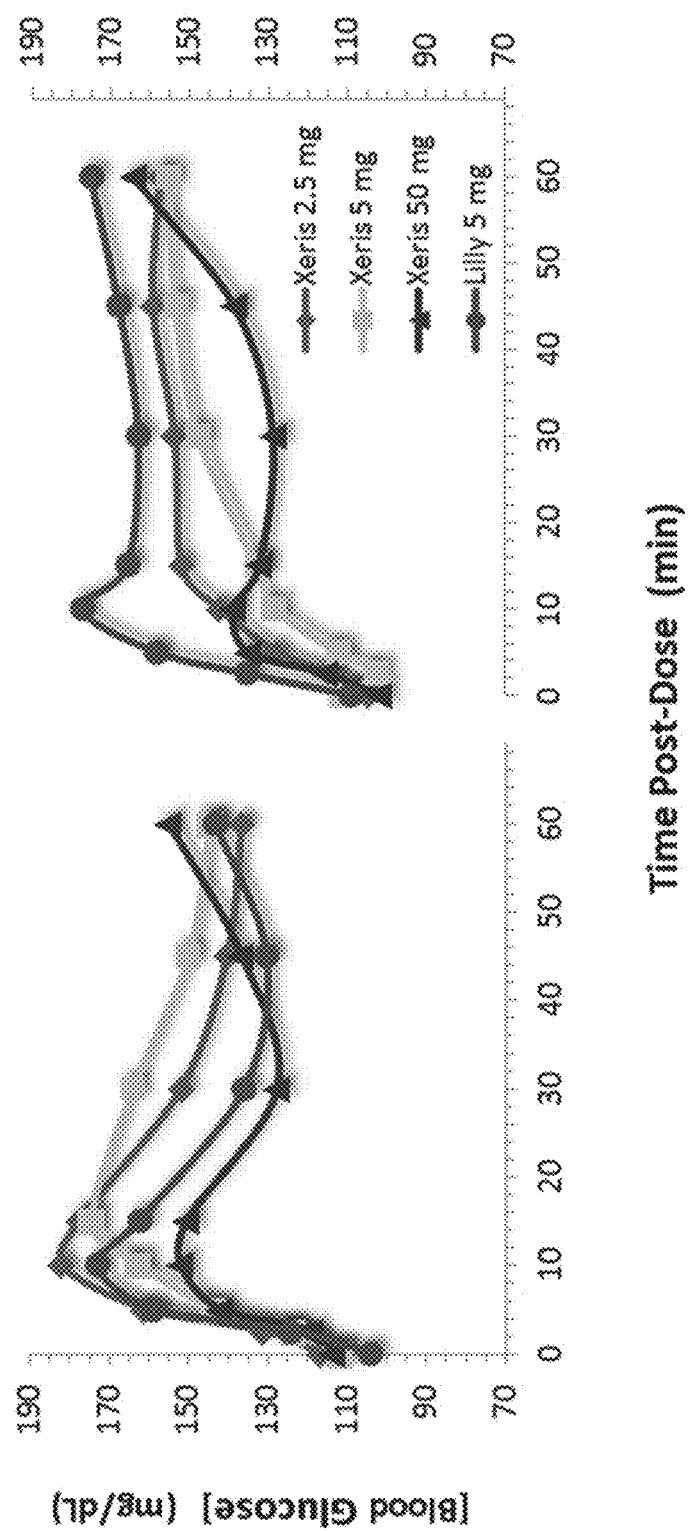
FIG. 5 illustrates blood glucose concentration-time profiles in male and female glucagon treatment groups with a Xeris Glucagon and a Lilly Glucagon.

Mean blood glucose levels rose significantly (p<0.0001) as early as 5 min post-dose), and remained significantly (p<0.0001) elevated relative to t=0 from 5 min post-dose until study termination 60 min post-dose (FIG. 4). At the termination of the study 60 min post-dosing, the blood glucose concentrations for all groups resulting from SC injection of glucagon were 144±4 mg/dL for male rat (95% Confidence Interval, 137 mg/dL to 151 mg/dL) and 163±3 mg/dL for female rat (95% Confidence Interval, 157 mg/dL to 170 mg/dL) groups from their corresponding baseline, t=0 pre-treatment levels of 112±2 mg/dL (95% Confidence Interval 108 mg/dL to 117 mg/dL) and 106±3 mg/dL (95% Confidence Interval, 101 mg/dL to 111 mg/dL; FIG. 5). Whereas the increase in blood glucose concentrations measured at 2.5 min post-dose was not significant for any one treatment group (p=0.2343), the increase in blood glucose level during the 2.5 min to 5 min interval, and from the 5 min to 10 min interval was significant (p<0.0001 and p=0.0176, respectively). At the 10 min period post-treatment, the mean blood glucose level of the 50 µg Xeris Glucagon treatment group was significantly lower (p=0.0359) than the blood glucose concentration resulting from SC injection with 5 µg Lilly Glucagon (FIG. 4). Whereas the blood glucose concentrations secondary to SC injection with 2.5 µg Xeris Glucagon were similar (p>0.05) to the blood glucose levels observed in the 5 µg Lilly Glucagon-treatment group over the time course of the study, SC injection with 5 µg Xeris Glucagon resulted in significantly lower blood glucose concentrations at 5 min (p=0.0003) and 10 min (p=0.0005) post-dosing when compared with those time periods resulting from injection of 5 µg Lilly Glucagon (FIG. 4).

The blood glucose concentration profiles over time for individual male (LEFT) and female (RIGHT) glucagon treatment cohorts is further shown in FIG. 5 and Table 16.

TABLE 16

| Treatment Group | Gender | Time Post-Dose (min) | [Blood Glucose] (mg/dL) | |
|---|---|---|---|---|
| | | | Mean | SEM |
| 2.5 µg Xeris Glucagon | Male | 0 | 117 | 3 |
| | | 2.5 | 131 | 9 |
| | | 5 | 161 | 1 |
| | | 10 | 182 | 8 |
| | | 15 | 177 | 11 |
| | | 30 | 152 | 6 |
| | | 45 | 140 | 3 |
| | | 60 | 137 | 5 |

TABLE 16-continued

| Treatment Group | Gender | Time Post-Dose (min) | [Blood Glucose] (mg/dL) Mean | SEM |
|---|---|---|---|---|
| 2.5 µg Xeris Glucagon | Female | 0 | 105 | 3 |
| | | 2.5 | 115 | 5 |
| | | 5 | 128 | 7 |
| | | 10 | 142 | 8 |
| | | 15 | 152 | 8 |
| | | 30 | 154 | 7 |
| | | 45 | 160 | 5 |
| | | 60 | 158 | 4 |
| 5 µg Xeris Glucagon | Male | 0 | 112 | 6 |
| | | 2.5 | 123 | 5 |
| | | 5 | 144 | 7 |
| | | 10 | 163 | 7 |
| | | 15 | 174 | 10 |
| | | 30 | 164 | 7 |
| | | 45 | 150 | 5 |
| | | 60 | 145 | 8 |
| 5 µg Xeris Glucagon | Female | 0 | 110 | 3 |
| | | 2.5 | 103 | 5 |
| | | 5 | 112 | 5 |
| | | 10 | 130 | 6 |
| | | 15 | 135 | 4 |
| | | 30 | 148 | 4 |
| | | 45 | 155 | 6 |
| | | 60 | 155 | 7 |
| 50 µg Xeris Glucagon | Male | 0 | 114 | 3 |
| | | 2.5 | 119 | 7 |
| | | 5 | 142 | 12 |
| | | 10 | 152 | 15 |
| | | 15 | 150 | 14 |
| | | 30 | 128 | 5 |
| | | 45 | 137 | 4 |
| | | 60 | 155 | 8 |
| 50 µg Xeris Glucagon | Female | 0 | 102 | 5 |
| | | 2.5 | 116 | 8 |
| | | 5 | 135 | 11 |
| | | 10 | 139 | 9 |
| | | 15 | 132 | 6 |
| | | 30 | 129 | 4 |
| | | 45 | 139 | 3 |
| | | 60 | 164 | 4 |
| 5 µg Lilly Glucagon | Male | 0 | 107 | 5 |
| | | 2.5 | 121 | 8 |
| | | 5 | 159 | 12 |
| | | 10 | 173 | 16 |
| | | 15 | 160 | 15 |
| | | 30 | 133 | 9 |
| | | 45 | 141 | 6 |
| | | 60 | 141 | 6 |
| 5 µg Lilly Glucagon | Female | 0 | 109 | 7 |
| | | 2.5 | 136 | 8 |
| | | 5 | 159 | 12 |
| | | 10 | 178 | 11 |
| | | 15 | 166 | 7 |
| | | 30 | 163 | 8 |
| | | 45 | 168 | 8 |
| | | 60 | 175 | 7 |

A comparison of blood glucose concentrations for all glucagon treated groups showed no significant differences by gender ($p<0.0771$). However, the blood glucose levels during the time course of the study were significantly different between the glucagon-treated male and female cohorts at 5 min ($p=0.0026$), 10 min ($p=0.0005$), 15 min ($p=0.0006$), 45 min ($p=0.0059$) and 60 min ($p=0.0007$) post-administration (FIG. 5). Further, the blood glucose concentrations were significantly different between males and females within treatment groups injected SC with either Xeris Glucagon (2.5 µg at 5, 10 and 15 min post-dose, $p \leq 0.0073$; 5 µg at 5, 10 and 15 min post-treatment, $p \leq 0.0009$) or with 5 µg Lilly Glucagon ($p \leq 0.0087$ at 45 and 60 min post-dose; FIG. 5).

The $BG_{max}$ for the groups injected SC with 2.5 µg Xeris Glucagon or 5 µg Xeris Glucagon was similar to that observed with SC injection of 5 µg Lilly Glucagon ($p=0.2908$ and $p=0.6974$, respectively; Table 16. Whereas no statistically significant differences in $BG_{max}$ were found by gender ($p=0.1460$) or by gender within group ($p=0.1790$), female rats dosed with Xeris Glucagon exhibited lower $BG_{max}$ levels when compared with male rats of any one treatment group, and these $BG_{max}$ levels were lower than that observed with SC injection of 5 µg Lilly Glucagon (Table 16). The glucose response declined from $BG_{max}$ to the last time period studied post-injection (60 min), and was similar between the 2.5 µg Xeris Glucagon ($p=0.8597$) or 5 µg Xeris Glucagon ($p=0.4582$) groups and the 5 µg Lilly Glucagon treatment group, but remained above the baseline t=0 pre-treatment level for all treatment groups at study termination ($p \leq 0.0005$).

The time of maximal glucose concentration ($TBG_{max}$) of the 5 µg Xeris Glucagon treatment group was equivalent ($p=0.2086$) to that derived from the 5 µg Lilly Glucagon treatment group (Table 16) However, dosing with 50 µg Xeris Glucagon gave rise to a higher $TBG_{max}$ than did SC injection with either 2.5 µg Xeris glucagon ($p=0.0218$) or 5 µg Lilly Glucagon ($p=0.0072$). The $TBG_{max}$ for female rats was delayed ($p>0.087$) in comparison to that of male rats for any one treatment group (Table 17) and only female rats treated with 2.5 µg Xeris Glucagon showed a significantly prolonged $TBG_{max}$ ($p=0.0007$) relative to their male rat counterparts within the same treatment group (Table 17) $TBG_{max}$ did not satisfy the Anderson-Darling test for normality ($p<0.0005$). However, the normal probability plot was linear with the data clustering at the various time points. Therefore, ANOVA was used to compare the mean $TBG_{max}$ by treatment group and gender.

TABLE 17

| Treatment Group | Gender | $BG_{max}$ (mg/dL) Mean | SEM | 95% CI | $TBG_{max}$ (min) Mean | SEM | 95% CI |
|---|---|---|---|---|---|---|---|
| 2.5 µg Xeris Glucagon | Male | 193 | 9 | 173-213 | 11.5 | 1.3 | 8.6-14.4 |
| | Female | 165 | 6 | 151-179 | 43.3 | 6.3 | 28.7-58.0 |
| 5 µg Xeris Glucagon | Male | 182 | 8 | 163-201 | 25.0 | 6.1 | 11.3-38.7 |
| | Female | 163 | 5 | 152-175 | 40.6 | 7.1 | 24.2-56.9 |
| 50 µg Xeris Glucagon | Male | 170 | 12 | 142-197 | 39.5 | 7.5 | 22.5-56.5 |
| | Female | 169 | 6 | 156-182 | 53.0 | 5.5 | 40.5-65.5 |

TABLE 17-continued

| Treatment Group | Gender | BG$_{max}$ (mg/dL) Mean | SEM | 95% CI | Mean | SEM | 95% CI |
|---|---|---|---|---|---|---|---|
| 5 µg Lilly Glucagon | Male | 185 | 15 | 150-221 | 17.2 | 5.9 | 3.6-30.8 |
|  | Female | 195 | 8 | 177-212 | 33.0 | 8.1 | 14.6-51.4 |

AUC$_{(0-60\ min)}$, MAE and T$_{MAE}$ Post-Glucagon Dosing. Whereas SC dosing with 2.5 µg Xeris Glucagon or with 5 µg Xeris Glucagon showed an equivalent AUC$_{(0-60\ min)}$ to that of treatment with 5 µg Lilly Glucagon (p=0.7565 and p=0.4149, respectively; Table 17), subcutaneous administration of 50 µg Xeris Glucagon resulted in a significantly lower (p=0.0482) AUC$_{(0-60\ min)}$ when compared with the AUC$_{(0-60\ min)}$ of the 5 µg Lilly Glucagon treatment group (Table 18). Subcutaneous injection of glucagon resulted in equivalent (p=0.8114) AUC$_{(0-60\ min)}$ between male and female cohorts within each treatment group (Table 18).

TABLE 18

| Treatment Group | Gender | AUC$_{(0-60\ min)}$ Mean | SEM | 95% CI |
|---|---|---|---|---|
| 2.5 µg Xeris Glucagon | Male | 9,165 | 261 | 8,576-9,754 |
|  | Female | 9,010 | 340 | 8,226-9,795 |
| 5 µg Xeris Glucagon | Male | 9,334 | 318 | 8,614-10,053 |
|  | Female | 8,495 | 163 | 8,120-8,874 |
| 50 µg Xeris Glucagon [a] | Male | 8,370 | 429 | 7,400-9,340 |
|  | Female | 8,186 | 192 | 7,746-8,626 |
| 5 µg Lilly Glucagon | Male | 8,491 | 495 | 7,349-9,632 |
|  | Female | 9,896 | 373 | 9,053-10,739 |

[a] Significantly lower (p = 0.048) vs 5 µg Lilly Glucagon group

The maximum absolute excursion (MAE) profile of any one Xeris Glucagon-treated group was comparable to that achieved by administration of 5 µg Lilly Glucagon (P=0.0581; Table 19). There were no significant differences in the MAE by gender (p=0.4800) or between male and female rats by group (p=0.2299; Table 19). While the time to maximum absolute excursion (T$_{MAE}$) was likewise comparable (p=0.0653) between the Xeris Glucagon-treated groups and the Lilly Glucagon-treated group (Table 19), female rats within any one treatment group showed a significantly prolonged T$_{MAE}$ profile (p<0.0001) when compared with male rats of the same treatment group (Table 19).

TABLE 19

| Treatment Group | Gender | MAE Mean | SEM | 95% CI | T$_{MAE}$ Mean | SEM | 95% CI |
|---|---|---|---|---|---|---|---|
| 2.5 µg Xeris Glucagon | Male | 76.4 | 7.4 | 59.6-93.3 | 11.5 | 1.3 | 8.6-14.4 |
|  | Female | 60.2 | 5.96 | 46.5-74.0 | 43.3 | 6.3 | 28.7-58 |
| 5 µg Xeris Glucagon | Male | 70.1 | 10.3 | 46.8-93.4 | 25.0 | 6.1 | 11.3-38.7 |
|  | Female | 53.7 | 4.3 | 43.9-63.7 | 40.6 | 7.1 | 24.2-56.9 |
| 50 µg Xeris Glucagon | Male | 57.9 | 11.3 | 32.4-83.4 | 29.5 | 8.4 | 10.5-48.5 |
|  | Female | 66.9 | 4.7 | 56.3-77.5 | 53.0 | 5.5 | 40.5-65.5 |
| 5 µg Lilly Glucagon | Male | 78.6 | 11.8 | 51.5-105.7 | 17.2 | 5.9 | 3.6-30.8 |
|  | Female | 85.6 | 5.5 | 73.3-97.9 | 33.0 | 8.1 | 14.6-51.4 |

All of the compositions and/or methods disclosed and claimed herein can be made and executed without undue experimentation in light of the present disclosure. While the compositions and methods of this invention have been described in terms of some embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The invention claimed is:

1. A composition for parenteral administration consisting essentially of:
   (a) about 0.45 wt. % of a glucagon peptide which has been dried in a non-volatile glycine buffer, and wherein the glucagon peptide has a pH memory that is about equal to the pH of the glucagon peptide in the non-volatile buffer, wherein the pH memory is between 2.5 to 3.5;
   (b) about 92 wt. % to 96 wt. % of an aprotic polar solvent, wherein the peptide is solubilized in the aprotic polar solvent, and wherein the aprotic polar solvent is dimethyl sulfoxide (DMSO);
   (c) about 3 wt. % to 7 wt. % of trehalose;
   (d) glycine; and
   (e) optionally hydrochloric acid,
   wherein the moisture content of the composition is less than 5 wt. %.

2. The composition of claim 1, consisting of:
   (a) about 0.45 wt. % of the glucagon peptide;
   (b) about 92 wt. % to 96 wt. % of the DMSO;
   (c) about 3 wt. % to 7 wt. % of the trehalose;

(d) the glycine; and
(e) optionally hydrochloric acid,
wherein the moisture content of the composition is less than 5 wt. %.

* * * * *